United States Patent
Vishwakarma et al.

(10) Patent No.: US 12,040,055 B2
(45) Date of Patent: Jul. 16, 2024

(54) SECURELY ARCHIVING DIGITAL DATA IN DNA STORAGE AS BLOCKS IN A BLOCKCHAIN

(71) Applicant: EMC IP Holding Company LLC, Hopkinton, MA (US)

(72) Inventors: Rahul Vishwakarma, Bangalore (IN); Bing Liu, Tianjin (CN); Parmeshwr Prasad, Bangalore (IN); Parminder Singh Sethi, Punjab (IN)

(73) Assignee: EMC IP Holding Company LLC, Hopkinton, MA (US)

( * ) Notice: Subject to any disclaimer, the term of this patent is extended or adjusted under 35 U.S.C. 154(b) by 447 days.

(21) Appl. No.: 17/155,552

(22) Filed: Jan. 22, 2021

(65) Prior Publication Data

US 2022/0236886 A1  Jul. 28, 2022

(51) Int. Cl.
*G16B 50/30* (2019.01)
*G11C 13/02* (2006.01)

(52) U.S. Cl.
CPC .............. *G16B 50/30* (2019.02); *G11C 13/02* (2013.01)

(58) Field of Classification Search
None
See application file for complete search history.

(56) References Cited

PUBLICATIONS

Limbachiya Dixita, Gupta K Manish, 2015. Natural Data Storage: A Review on Sending Information from Now to Then ACM J. Emerg. Technol. Comput. Syst. V, N, Article A (Year: 2015).*

Ozercan et al. Realizing the potential of blockchain technologies in genomics. Genome Research 28:1255-1263 Published by Cold Spring Harbor Laboratory Press, 2018 (Year: 2018).*

Chen et al. Gencore: an efficient tool to generate consensus reads for error suppressing and duplicate removing of NGS dataBMC Bioinformatics 2019, 20(Suppl 23):606 (Year: 2019).*

Yixin Wang et al. High capacity DNA data storage with variable-length Oligonucleotides using repeat accumulate code and hybrid mapping. Journal of Biological Engineering (2019) 13:89 (Year: 2019).*

Yeongjae Choi et al. High information capacity DNA-based data storage with augmented encoding characters using degenerate bases. Scientific Reports (2019) 9:6582 (Year: 2019).*

Carlini F, Carlini R, Dalla Palma S, Pareschi R and Zappone F (2020) The Genesy Model for a Blockchain-Based Fair Ecosystem of Genomic Data. Front. Blockchain 3:483227. (Year: 2020).*

(Continued)

*Primary Examiner* — Larry D Riggs, II
*Assistant Examiner* — Mary C Leverett
(74) *Attorney, Agent, or Firm* — Staniford Tomita LLP

(57) ABSTRACT

Embodiments for storing digital data in DNA storage by receiving input file data, encoding the input file data into an oligonucleotide sequence to produce sequence data through a transformation of text to binary to Base_3 encoding, organizing the Base_3 sequence data into chunks of a defined chunk size, and storing the chunks in a block of a blockchain. The oligonucleotide sequence may comprise metadata for the input file data that refers to actual data stored in the DNA storage, where the actual data is formed by synthesizing the oligonucleotide sequence in a DNA synthesis process. The chunks may be stored in the blockchain only if the block agrees with a smart contract defined for the oligonucleotide sequence.

20 Claims, 14 Drawing Sheets

(56) References Cited

PUBLICATIONS

Yang Xu et al. Blockchain Empowered Arbitrable Data Auditing Scheme for Network Storage as a Service. IEEE Transactions on Services Computing, vol. 13, No. 2, Mar./Apr. 2020 (Year: 2020).*

Cogo, Vinicius, Joao Paulo, and Alysson Bessani. "Genodedup: Similarity-based deduplication and delta-encoding for genome sequencing data." IEEE Transactions on Computers 70.5 (2020): 669-681. (Year: 2020).*

* cited by examiner

SECURELY ARCHIVING DIGITAL DATA IN DNA STORAGE AS BLOCKS IN A BLOCKCHAIN

TECHNICAL FIELD

Embodiments are generally directed to data storage networks, and more specifically to storing digital data in DNA storage using blockchain and smart contract technology.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

To accommodate the overwhelming amount of data that is being generated and stored, advanced storage techniques such as DNA data storage are being developed. As is known, DNA consists of double stranded polymers of four different nucleotides: adenine (A), cytosine (C), guanine (G) and thymine (T). The primary role of DNA is long-term storage of genetic information. This feature of DNA is analogous to a digital data sequence where two binary bits 0 and 1 are used to store the digital data. This analogous nature of DNA nucleotide with binary bits can be exploited to use artificial nucleotide data memory. DNA storage involves encoding and decoding binary data to and from synthesized strands of DNA. It is characterized by high storage density, but also imposes high costs and suffers from slow access (read/write) times.

Recent developments in the synthesis of DNA has significantly reduced the price of per base pair (DBA-Based unit of storage); however, in current systems, the price per base pair remains USD $0.07, which is far from commercial implementation as compared to HDD or SSD based storage costs. Much research and development work for DNA storage has been focused on designing a data encoding method for DNA-based storage, error correction code, genomic compression, enzymatic method of synthesizing nucleotides in lab, and so on, with little effort spent on the actual encryption of the DNA stored data. Even less work has been done in reducing the amount of nucleotide material required for digital information representation and reducing the storage cost per unit of storage for real time use.

Accordingly, several noticeable problems from the in-silico perspective remain, including: efficient encoding of data type (text, image, binary files), random access, effective deduplication for genomic data (compression is not effective), overcoming high storage costs, eliminating single points of failure in traditional DNA-based storage, and the fact that DNA-encoded data is currently not resistant to malicious tampering.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

INCORPORATION BY REFERENCE

Each publication, patent, and/or patent application mentioned in this specification is herein incorporated by reference in its entirety to the same extent as if each individual publication and/or patent application was specifically and individually indicated to be incorporated by reference.

BRIEF DESCRIPTION OF THE DRAWINGS

In the following drawings like reference numerals designate like structural elements. Although the figures depict various examples, the one or more embodiments and implementations described herein are not limited to the examples depicted in the figures.

DETAILED DESCRIPTION

Figure 1:
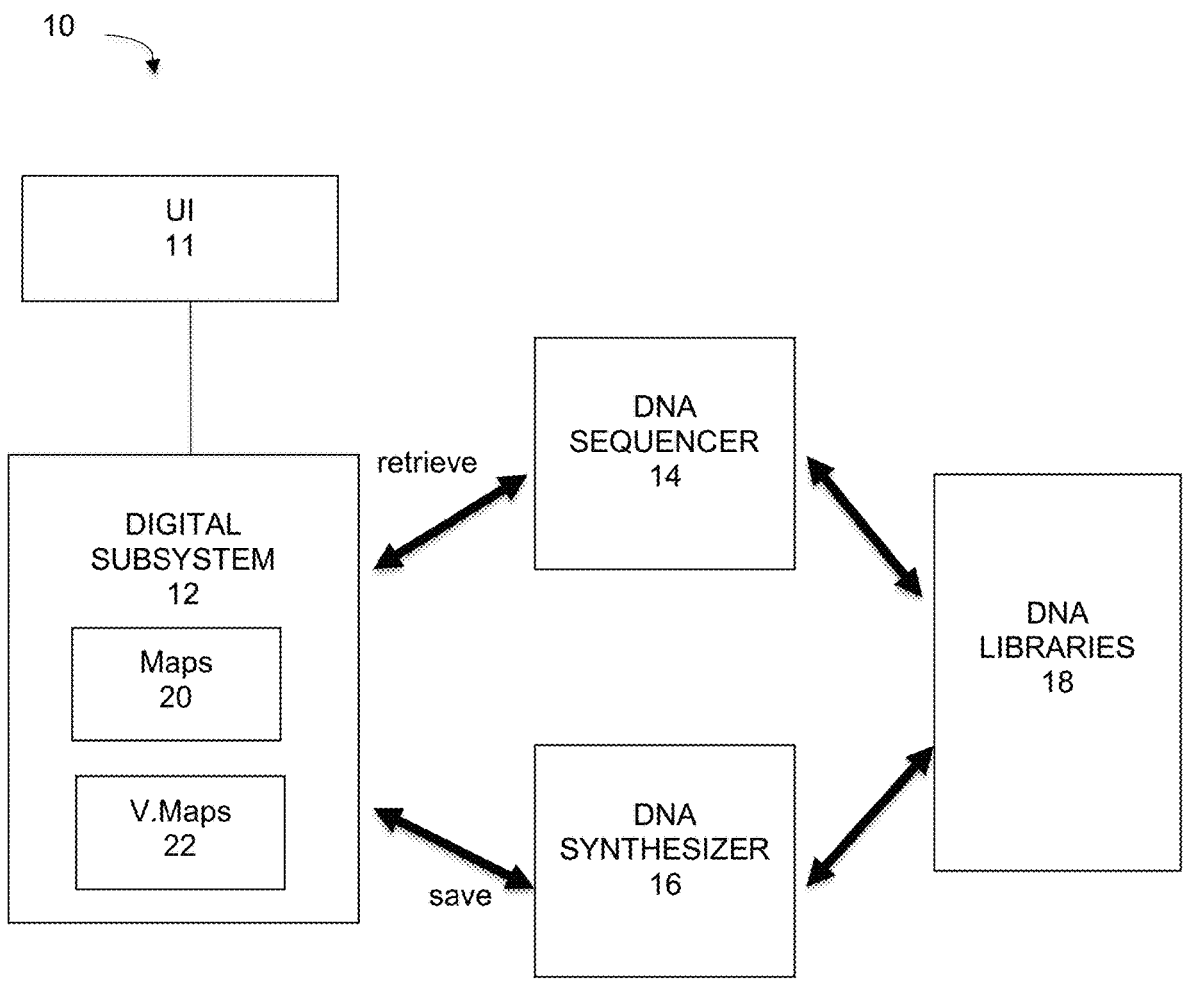
FIG. 1 is a block diagram illustrating a system for storing and retrieving data using DNA storage, under some embodiments.

A detailed description of one or more embodiments is provided below along with accompanying figures that illustrate the principles of the described embodiments. While aspects of the invention are described in conjunction with such embodiments, it should be understood that it is not limited to any one embodiment. On the contrary, the scope is limited only by the claims and the invention encompasses numerous alternatives, modifications, and equivalents. For the purpose of example, numerous specific details are set forth in the following description in order to provide a thorough understanding of the described embodiments, which may be practiced according to the claims without some or all of these specific details. For the purpose of clarity, technical material that is known in the technical fields related to the embodiments has not been described in detail so that the described embodiments are not unnecessarily obscured.

It should be appreciated that the described embodiments can be implemented in numerous ways, including as a process, an apparatus, a system, a device, a method, or a computer-readable medium such as a computer-readable storage medium containing computer-readable instructions or computer program code, or as a computer program product, comprising a computer-usable medium having a computer-readable program code embodied therein. In the context of this disclosure, a computer-usable medium or computer-readable medium may be any physical medium that can contain or store the program for use by or in connection with the instruction execution system, apparatus or device. For example, the computer-readable storage medium or computer-usable medium may be, but is not limited to, a random-access memory (RAM), read-only memory (ROM), or a persistent store, such as a mass storage device, hard drives, CDROM, DVDROM, tape, erasable programmable read-only memory (EPROM or flash memory), or any magnetic, electromagnetic, optical, or electrical means or system, apparatus or device for storing information. Alternatively, or additionally, the computer-readable storage medium or computer-usable medium may be any combination of these devices or even paper or another suitable medium upon which the program code is printed, as the program code can be electronically captured, via, for instance, optical scanning of the paper or other medium, then compiled, interpreted, or otherwise processed in a suitable manner, if necessary, and then stored in a computer memory. Applications, software programs or computer-readable instructions may be referred to as components or modules. Applications may be hardwired or hard-coded in hardware or take the form of software executing on a general-purpose computer or be hardwired or hard-coded in hardware such that when the software is loaded into and/or executed by the computer, the computer becomes an apparatus for practicing the invention. Applications may also be downloaded, in whole or in part, through the use of a software development kit or toolkit that enables the creation and implementation of the described embodiments. In this specification, these implementations, or any other form that the invention may take, may be referred to as techniques. In general, the order of the steps of disclosed processes may be altered within the scope of the described embodiments.

Some embodiments of the invention involve large-scale IT networks or distributed systems (also referred to as "environments"), such as a cloud based network system or very large-scale wide area network (WAN), or metropolitan area network (MAN). However, those skilled in the art will appreciate that embodiments are not so limited, and may include smaller-scale networks, such as LANs (local area networks). Thus, aspects of the one or more embodiments described herein may be implemented on one or more computers in any appropriate scale of network environment, and executing software instructions, and the computers may be networked in a client-server arrangement or similar distributed computer network.

Embodiments are directed to systems and methods for reducing the cost to store DNA (or oligonucleotide sequence) data per unit of digital information. Such embodiments include features such as the use of trusted storage and random access of data, decentralized storage of immutable data/metadata in a blockchain, and the use of a smart contract for similarity-based data deduplication. The random access element is implemented through a key-value pair for locality similarity hashing (LSH). Similarity based variable-length deduplication with delta encoding for a genomic data (at the destination) is used to reduce the number of nucleotides for information representation, and storing metadata in a blockchain makes the data immutable and tamper proof thereby eliminating the single point of failure.

DNA Data Storage

In general, DNA digital storage stores data in the base sequence of DNA. The technology uses artificial DNA made using commercially available oligonucleotide sequencing machines for storage and DNA sequencing machines for retrieval. The basic process of a DNA storage pipeline is as follows:

Encoding→Synthesis→Storage→Retrieval→Sequencing→Decoding

Present methods and systems for implementing and storing data in DNA storage media may be used with embodiments described herein, as known by those of ordinary skill in the art As stated above, DNA consists of four types of nucleotides: A, C, G and T. A DNA strand, or oligonucleotide, is a linear sequence of these nucleotides. Oligonucleotides are short DNA or RNA molecules that are commonly made using solid-phase chemical synthesis and comprise small pieces of nucleic acids that can be manufactured as single stranded molecules with any user-specified sequence (e.g., AGGTCTATGCC, etc.). Encoding comprises converting binary digital data into a format for representation as DNA information. The encoding may be into any of several different well known formats, such as a quaternary (base-4) or a ternary (base 3) data format using, for example Huffman encoding, to use only three of the four nucleotides, and mapping the encoded format to DNA nucleotides which are synthesized chemically and stored as DNA strands. The DNA data is retrieved by sequencing the stored DNA to obtain the DNA strands, and decoding the DNA data to obtain the original data.

FIG. 1 is a block diagram illustrating a system for storing and retrieving data using DNA storage, under some embodiments. With reference to FIG. 1, system 10 may be a data center or part of a data center, or it may be a standalone system. For the example embodiment of FIG. 1, system 10 comprises a digital subsystem 12 and a DNA subsystem having a DNA sequencer 14, a DNA synthesizer 16, and DNA libraries 18 for storing DNA data. A user interface (UI) 11 interfaces with the digital subsystem 12 for inputting data for DNA storage and for retrieving data from DNA storage. The user interface 11 may include application programming interfaces (APIs) to connect users to system 12 through an enterprise network, and subsystem 12 may comprise a Data Domain Restorer (DDR) for deduplicating data along with other processing and storage resources, as shown in and described below with respect to system 100 of FIG. 2.

In an embodiment, system 10 encoding and decoding operations transform the digital binary data to and from the representations used by DNA storage. The digital subsystem 12 may include storage for metadata such as maps 20 and virtual maps 22 for mapping the digital data to the DNA data. The DNA sequencer 14 may be a commercially available synthesizer for synthesizing artificial DNA for storage in DNA libraries 18, and DNA sequencer 16 may be a commercially available sequencer for retrieving the DNA sequences stored in the DNA libraries. Both or either of the sequencer and synthesizer may be controlled by the system 10 to sequence and synthesize the DNA sequence.

The basic storage component in system 10 is a DNA strand, which has the core components of primer sites, identifier, address, and data block. The primer sites amplify the strand to allow random access capability and are preferably located on both ends of a strand. The identifier is a key that identifies the DNA data. The address specifies the location of the data object for restoring the data object correctly, and the data block comprises a block of data from the data object. A data object may be divided into many DNA strands because the functional length (presently) of a DNA strand is on the order of 100-200 nucleotides, which makes it possible to store 50-100 bits. Overlapping DNA strands may be generated for redundancy and the address is used to identify the position of the data block in the data object.

The DNA storage libraries 18 comprise DNA strands stored in liquid pools in well plates to store the actual DNA fragments. The libraries may comprise a primary map library, a hash map library, and a data library, or any other library composition. The key/hash/data objects are the actual information stored in each library and are obtained when sequencing is performed. The hash and data objects include the unique identifier (UID) as the identifier to verify sequencing. The UID differentiates between files with the same hash but different data. When a new file is saved, if its hash already exists and the data of the old and new objects is the same, then the new file gets the same UID; however, if the data is different, the new file gets a new UID. Storage and retrieval of DNA data using a library mapping system, such as shown in FIG. 1 may be performed in any appropriate manner, such as that described in U.S. application Ser. No. 15/960,945 entitled "DNA-Based Data Center with Deduplication Capability," which is assigned to the assignee of the present application, and which is incorporated herein by reference in its entirety.

With respect to advantages, DNA storage provides a high degree of data density of compactness. Most recent research suggest a theoretical bound of storage up to 215 petabytes in only one gram (1 gm) of DNA. Present technology practically allows reaching up to 85% utilization of this bound, which is up to 1000 times more compact compared to current magnetic media. It also features a significant longevity and survival rate. Most advanced research suggests that a DNA sequence may survive 2000 years if stored at 10 degrees Celsius and up to 1 million years if stored at −18 degrees Celsius. It also features superior energy savings. Research suggests up to $10^8$ less energy spent in the process of DNA storage compared to magnetic storage. Against these benefits are certain disadvantages. First is cost, where the estimated cost of the method is currently around $7,000 per 2 MB encoding and $2,000 for decoding the same 2 MB. Another is a lack of basic memory related technologies (e.g., compression, advanced error handling, deduplication, etc.), which are all essential for industrial storage standards. Third is the slow and semi-manual retrieval process that requires applying DNA sequencing processes.

Thus, DNA storage is generally much more compact than current tape and disk drive storage systems, and provides tremendous capacity and great longevity. These features have led researchers to call this method of data storage "apocalypse-proof." As stated above, however, a significant disadvantage of DNA storage is that data retrieval can be a very slow process, as the DNA needs to be sequenced in order to retrieve the data. Thus, the method best used for data with very low access rate. Furthermore, because it is so costly, it is best reserved for only the most valuable data. With respect to specific benefits and disadvantages of DNA storage, data that is eligible or most appropriate to be stored in DNA storage thus has certain key characteristics. These characteristics (among others) can be listed as follows: (1) limited volume per the data protection policy configurations (e.g., the data must conform with strict batch sizes defined by set policies); (2) low to no access rate (e.g., data that is used once at a pre-defined future date or data that will be used only in the case of catastrophe that has terminated all other backups/replications of the data; (3) extremely high valued data based on existing data valuation algorithms and most suitable to the databases; and (4) high radius of recovery (ROR), where the radius of recovery reflects how many additional existing assets can be fully or partially retrieved from this data. For purposes of discussion, data that fits these characteristics is referred to herein as Apocalypse Day Data (ADD).

Figure 2:
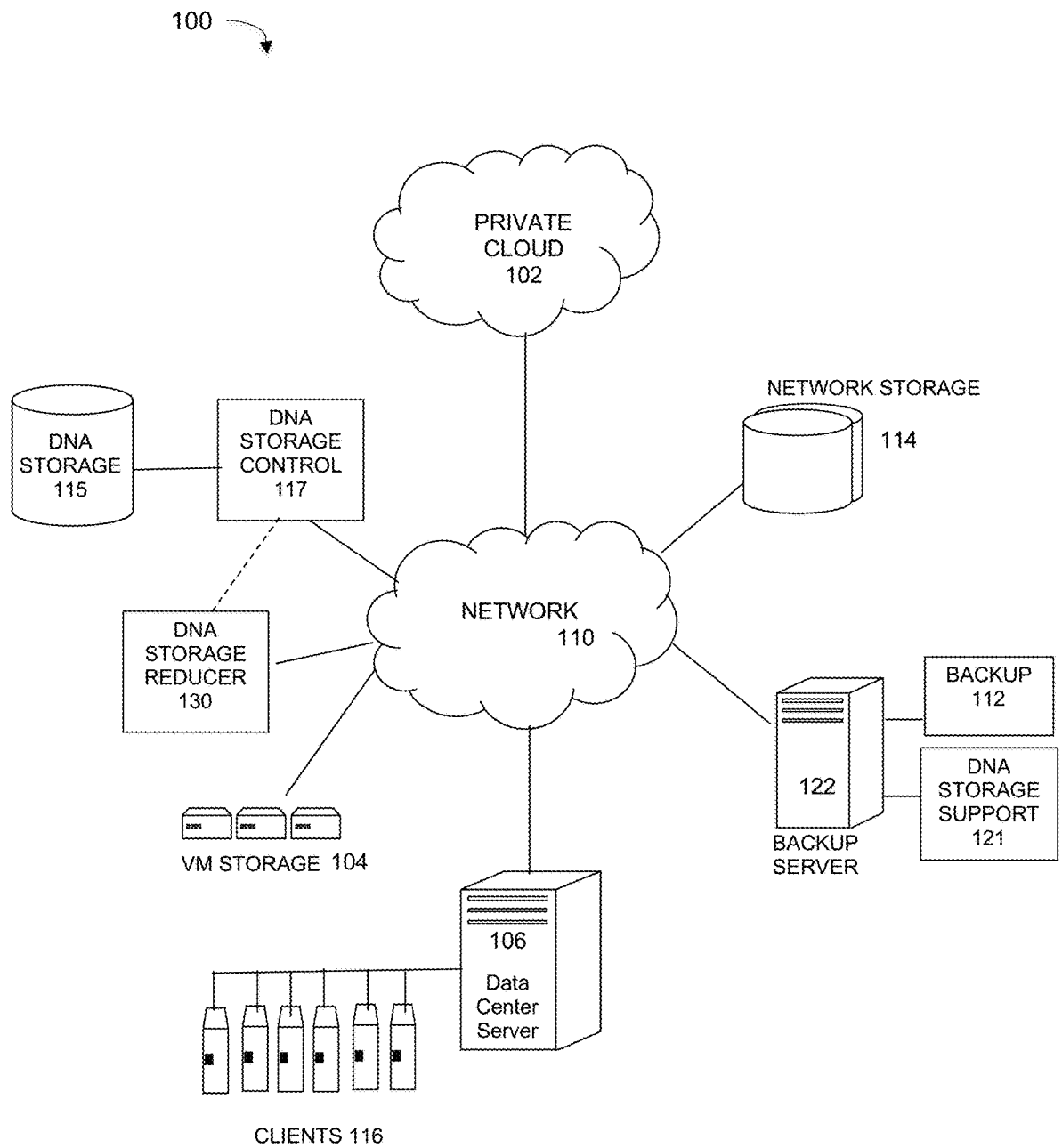
FIG. 2 illustrates an enterprise-scale network system with devices that implement one or more embodiments of a data protection system for DNA storage and support, under some embodiments.

FIG. 2 illustrates an enterprise data protection system that implements DNA data storage and support processes under some embodiments. For the example network environment 100 of FIG. 1, a backup server 122 executes a backup management process 112 that coordinates or manages the backup of data from one or more data sources, such as other servers/clients to storage devices, such as network storage 114 and/or virtual storage devices 104. With regard to virtual storage 104, any number of virtual machines (VMs) or groups of VMs (e.g., organized into virtual centers) may be provided to serve as backup targets. The VMs or other network storage devices serve as target storage devices for data backed up from one or more data sources, which may have attached local storage or utilize networked accessed storage devices 114.

The network server computers are coupled directly or indirectly to the target VMs, and to the data sources through network 110, which is typically a cloud network (but may also be a LAN, WAN or other appropriate network). Network 110 provides connectivity to the various systems, components, and resources of system 100, and may be implemented using protocols such as Transmission Control Protocol (TCP) and/or Internet Protocol (IP), well known in the relevant arts. In a cloud computing environment, network 110 represents a network in which applications, servers and data are maintained and provided through a centralized cloud computing platform. In an embodiment, system 100 may represent a multi-tenant network in which a server computer runs a single instance of a program serving multiple clients (tenants) in which the program is designed to virtually partition its data so that each client works with its own customized virtual application, with each VM representing virtual clients that may be supported by one or more servers within each VM, or other type of centralized network server.

The data generated or sourced by system 100 may be stored in any number of persistent storage locations and devices, such as local client or server storage. The storage devices represent protection storage devices that serve to protect the system data through the backup process. Thus, backup process 112 causes or facilitates the backup of this data to the storage devices of the network, such as network storage 114, which may at least be partially implemented through storage device arrays, such as RAID components. In an embodiment network 100 may be implemented to provide support for various storage architectures such as storage area network (SAN), Network-attached Storage (NAS), or Direct-attached Storage (DAS) that make use of large-scale network accessible storage devices 114, such as large capacity disk (optical or magnetic) arrays. The data sourced by the data source (e.g., DB server 106) may be any appropriate data, such as database data that is part of a database management system within a data center comprising a server 106 and clients 116, and the data may reside on one or more hard drives (e.g., 114) for the database(s) in a variety of formats.

As stated above, the data generated or sourced by system 100 and transmitted over network 110 may be stored in any number of persistent storage locations and devices, such as local client storage, server storage, or other network storage. In a particular example embodiment, system 100 may represent a Data Domain Restorer (DDR)-based deduplication storage system, and backup server 122 may be implemented as a DDR Deduplication Storage server provided by Dell-EMC Corporation. However, other similar backup and storage systems are also possible.

Although embodiments are described and illustrated with respect to certain example implementations, platforms, and applications, it should be noted that embodiments are not so limited, and any appropriate network supporting or executing any application may utilize aspects of the root cause analysis process described herein. Furthermore, network environment 100 may be of any practical scale depending on the number of devices, components, interfaces, etc. as represented by the server/clients and other elements of the network. For example, network environment 100 may include various different resources such as WAN/LAN networks and cloud networks 102 are coupled to other resources through a central network 110.

FIG. 2 generally represents an example of a large-scale IT operation environment that contains a large number of assets required by the business for daily operations. It also represents a data storage system having components that work to facilitate storage of appropriate data in DNA storage devices 115. With respect to DNA storage, backup and recovery to and from DNA storage media 115 may be performed by a DNA storage controller 117. The control component 117 executes the storage of appropriate data onto DNA media of storage devices 115 using known processes of a DNA storage pipeline as described above. Such a pipeline may include artificial DNA media made using commercially available oligonucleotide synthesis machines for storage and DNA sequencing machines for retrieval, or other similar machines, such as nucleic acid memory (NAM) and others, as known to those of skill in the art.

As stated above, embodiments provide cost-effective storage of data assets that are classified as or considered to be most valuable. Such data is often referred to as "apocalypse day data" (ADD), and require the extreme reliability of DNA sequence storage as compared to storage on existing solid state, magnetic or optical storage drives. ADD data generally represents any data that is important enough to be put into the most expensive type of data storage, and/or that is to be kept safe and secure in an offline location and retrieved only in an event of a catastrophe. Examples of DNA storage mechanisms for ADD data are described in U.S. patent application Ser. No. 15/876,188 entitled "Automatic Identification, Definition and Management of Data for DNA Storage Systems," which is assigned to the assignee of the present application, and which is incorporated herein by reference in its entirety.

Although embodiments are described and illustrated primarily in conjunction with ADD data, it should be noted that embodiments are not so limited, and any type of digital data can be processed and stored in conjunction with embodiments described herein.

As stated above, storage costs of DNA data per base pair remains significantly above that of traditional HDD or even SSD based storage. Embodiments include methods for reducing the amount of nucleotide material required for digital information representation and reducing the storage cost per unit of storage for real time use. In an embodiment, system 100 of FIG. 2 includes a DNA storage reducer component 130 that may be incorporated as part of DNA storage control 117 and/or DNA storage support 121, or provided as a standalone process/component accessible through network 110. This component improves random access through key/value pairs for locality similarity hashing (LSH), reducing the number of nucleotides for data representation using similarity-based variable length deduplication with delta encoding at the destination, and storage of metadata in a blockchain for making the data immutable.

Such a process provides several advantages over present systems that are limited to file level deduplication at the source (e.g., DNA storage pools) and not at the destination, are centralized (single point of failure), and are not absolutely tamper proof. Embodiments of include the definition of a new data structure in which a blockchain is used wherein each block consists of metadata and data (nucleotide sequence), and the use of similarity-based deduplication (variable length) along with delta encoding as a Smart Contract for creating new blocks in the blockchain. Finding similarities between genomic data chunks (blocks) helps achieve high data reduction ratios and reduces the overall costs of DNA-based storage.

Blockchain and Smart Contracts

In an embodiment, certain DNA information (e.g., metadata) is stored in a blockchain. In general, a blockchain can include a history of data, messages, or transactions in a series of blocks where each block contains a mathematical summary, called a hash, of the previous block. This creates a blockchain where any changes made to a block will change that block's hash, which must be recomputed and stored in the next block. This changes the hash of the next block, which must also be recomputed and so on until the end of the chain. In the illustrated example, Block 0 has a hash "0x3a34ad . . . 55." The next Block 1 includes the hash "0xf6e1da2 . . . deb" and the previous (Block 0) hash "0x3a34ad . . . 55." The following Block 2 includes the hash "0x9327eb1b . . . 36a21" and the previous block's hash "0xf6e1da2 . . . deb."

The hash is based on a mathematical function that is not reversible and system users cannot predict what input can be used to produce the desired output. A valid hash can be found by repeatedly adjusting a changeable value in the block, which is known as a "nonce." The nonce can be adjusted and the hash can be recalculated until a valid hash is found that meets the validity requirements. The unpredictable nature of the hash considerably increases the difficulty of finding a nonce that produces a valid hash of the block. Typically, trillions of different nonce values may be tried before a valid hash is found. Therefore, changing the value of previously stored data in the blockchain can require a substantial amount of computational effort, although not impossible. The security of the blockchain is further enhanced by storing the blockchain data on a distributed network. A large number of users can have access to the blockchain network and miner nodes can be continuously attempting to add blocks to the end of the blockchain by finding a nonce that produces a valid hash for a given block of data.

Blockchains can be used with various types of transactions. For example, a transaction can use identity tokens for physical or digital assets. The identity tokens can be generated using a cryptographic hash of information that uniquely identifies the asset. The tokens can also have an owner that uses an additional public/private key pair. The owner of a public key can be set as the token owner identity and when performing actions against tokens, ownership proof can be established by providing a signature generated by the owner private key and validated against the public key listed as the owner of the token. The identity token for an entity may be the public key of a public/private key pair, where the private key is held by the entity. The creation of an identity token for an asset in a blockchain can establish a provenance of the asset, and the identity token can be used in transactions of the asset stored in a blockchain, creating a full audit trail of the transactions.

To record a simple transaction in a blockchain, each party and asset involved with the transaction needs an account that is identified by a digital token. For an asset transfer, for example, a current owner and next owner create accounts, and the current owner also creates an account that is uniquely identified by an asset identification number. The account for the asset identifies the current owner. The current asset owner creates a transaction against the account for the asset that indicates: 1) the transaction is a transfer of ownership, 2) the public keys (i.e., identity tokens) of the current owner and the next owner, 3) the identity token of the physical asset, and 4) the transaction is signed by the private key of the current owner. The current owner of the asset can create a transaction request that includes the transaction information on a user interface of a computing device. The transaction request can be broadcast to the blockchain network. If the blockchain network of nodes does not validate the transaction, the transaction is stopped and the transfer of ownership is not recorded. If the blockchain network of nodes validates and verifies the transaction, the transaction is combined with other transactions occurring at the same time to form data for a new block and the new block is added to the blockchain. The recorded transaction in the blockchain is evidence that the next owner identified in the transaction request is now the current owner.

To enable more complex transactions, a blockchain system can use "smart contracts" which is computer code that implements transactions of a contract. The computer code may be executed in a secure platform that supports recording transactions in blockchains. In addition, the smart contract itself can be recorded as a transaction in the blockchain using an identity token that is a hash of the computer code so that the computer code that is executed can be authenticated. When deployed, a constructor of the smart contract executes initializing the smart contract and its state. The state of a smart contract is stored persistently in the blockchain. When a transaction is recorded against a smart contract, a message is sent to the smart contract and the computer code of the smart contract executes to implement the transaction. The computer code ensures that all the terms of the contract are complied with before the transaction is recorded in the blockchain. For example, a smart contract may support the sale of an asset. The inputs to a smart contract to sell the asset may be the identity tokens of the seller, the buyer, and the asset and the sale price. The computer code ensures that the seller is the current owner of the asset and that the buyer has sufficient funds in their account. The computer code then records a transaction that transfers the ownership of the asset to the buyer and a transaction that transfers the sale price from the buyer's account to the seller's account. If either transaction is not successful, neither transaction is recorded in the blockchain.

When a message is sent to a smart contract to record a transaction, the message is sent to each node that maintains a replica of the blockchain. Each node can execute the computer code of the smart contract to implement the transaction. For example, if all nodes each maintain a replica of a blockchain, then the computer code is executed at each of the nodes. When a node completes the execution of the computer code, the results of the transaction are recorded in the blockchain. The nodes can employ a consensus algorithm to decide on which transactions to record and which transactions to discard. A majority of the nodes must verify the transaction, in order for the transaction to be recorded on the blockchain. The execution of the computer code at each node helps ensure the authenticity of the blockchain.

Figure 3A:
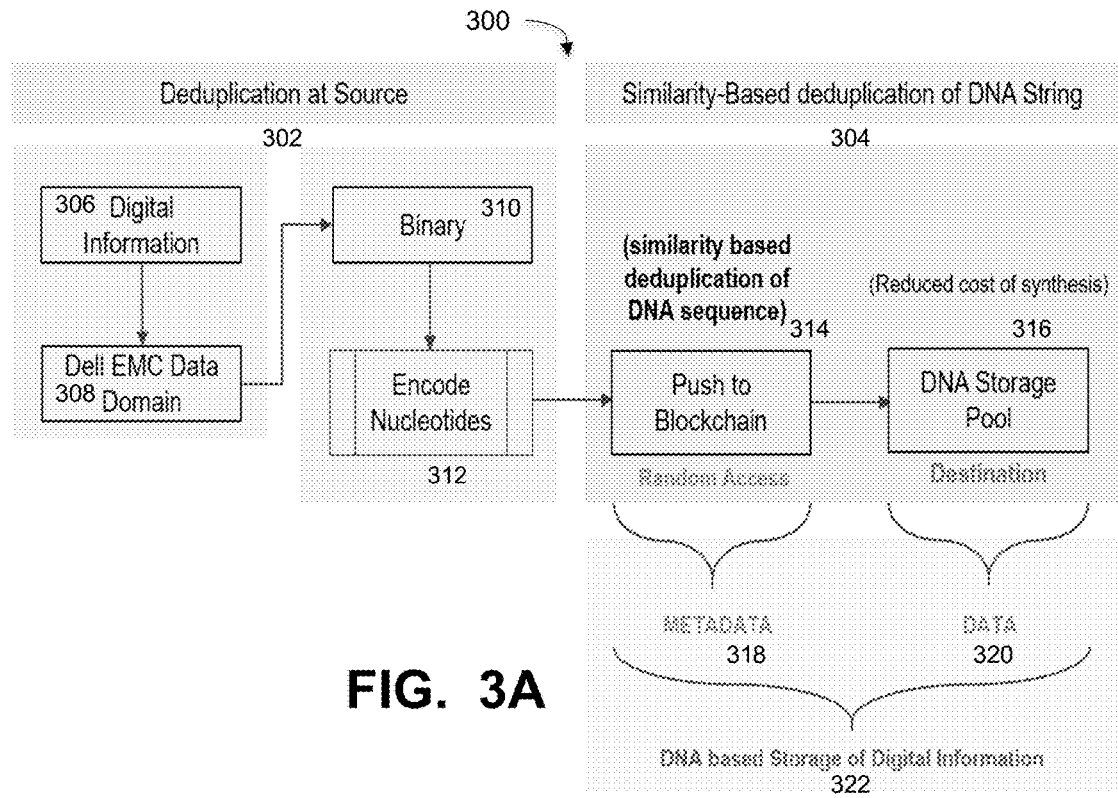
FIG. 3A illustrates a system of creating metadata for storing DNA data, under some embodiments.

FIG. 3A illustrates a system 300 for creating metadata for storing DNA data, under some embodiments. As shown in FIG. 3A, digital data 306 is deduplicated at a source site 302 using a deduplication engine 308, which may be a Data Domain appliance or similar. The deduplication engine deduplicates the incoming data streams to produce binary code 310, which is then encoded into nucleotides, as described at least in part above. Embodiments include a newly defined data structure for storing data as a block in a blockchain. System 300 also includes a destination site 304 that performs similarity-based deduplication of the encoded DNA strings. In an embodiment, the system provides a method of creating metadata 318 for storing digital information in oligonucleotides of the DNA string and store the deduplicated nucleotides sequences in a DNA storage pool 318. The encoded DNA string are pushed to blockchain 314 for performing similarity-based deduplication at the destination 304. The blockchain stores only metadata 318, and a new block in blockchain will be created only based on the deduplication across all existing blocks of the blockchain. A smart contract is used for the deduplication. The similarity-based deduplication uses variable length, specific to triplet codons. Deduplication generally provides better read performance as compared to compression. The combination of the metadata 318 and the data 320 comprises the DNA based storage 322 of the original digital information 306.

Figure 3B:
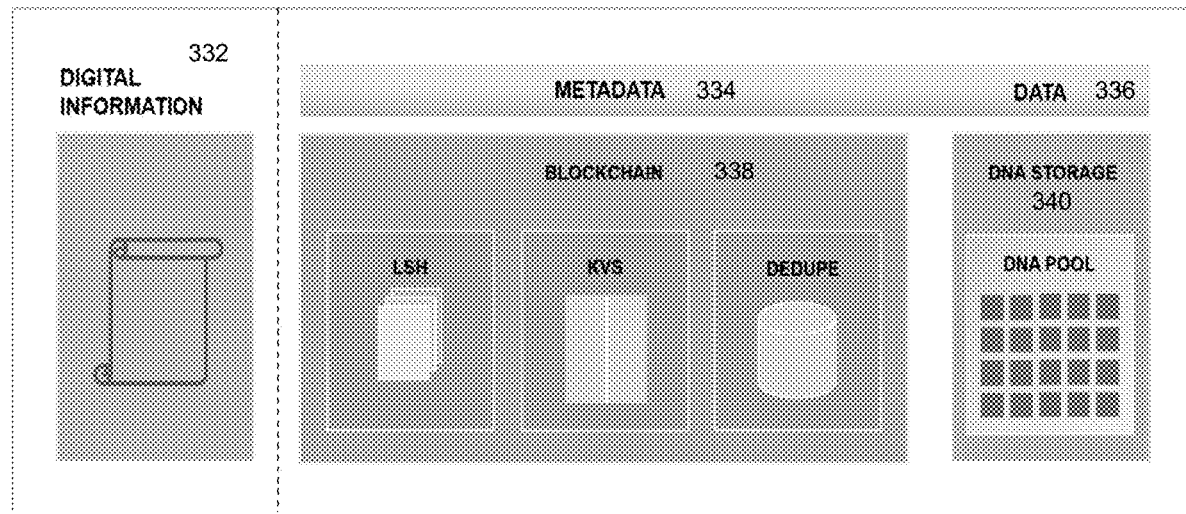
FIG. 3B illustrates a composition of digital data stored in blockchain metadata and DNA stored data, under some embodiments.
Figure 3C:
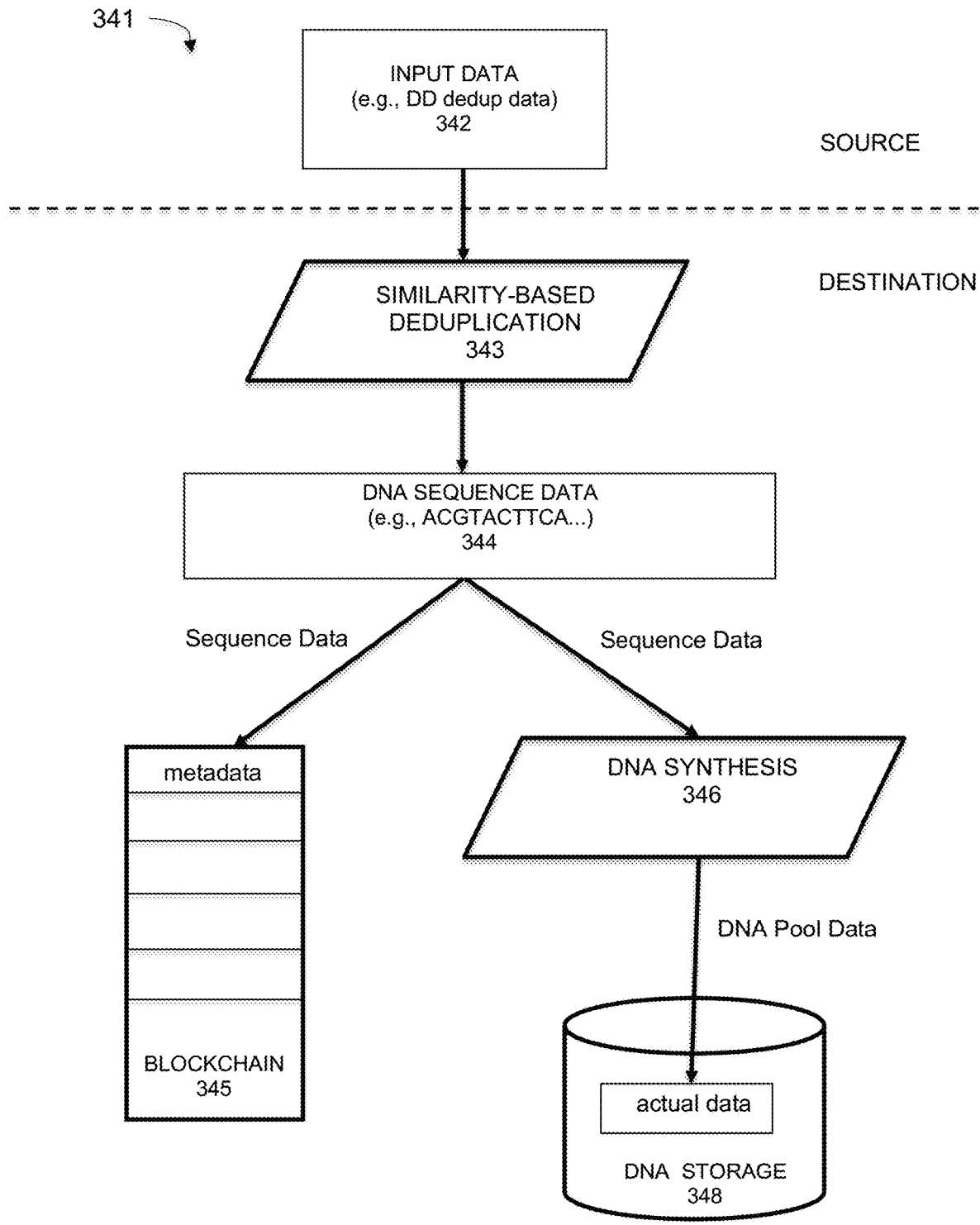
FIG. 3C illustrates the composition of the metadata and data processed in system 300 of FIG. 3A, under some embodiments.

Embodiments include a newly defined data structure for storing data as a block in a blockchain, where the overall stored data comprises metadata and data in the form of a nucleotide sequence. FIG. 3C illustrates the composition of the metadata and data processed in system 300 of FIG. 3A, under some embodiments. The input data 342 for process 341 comprises original source data sent to be stored by a backup process, such as Data Domain deduplicated data.

This data is input to a similarity-based deduplication process 343 on the backup destination side, which produces a sequence of DNA strings (DNA or oligonucleotide sequence) 344. This sequence of DNA strings obtained after the similarity-based deduplication is stored in a block of the blockchain 345, and constitutes the 'metadata' of the system. The same DNA sequence 344 is synthesized in DNA synthesis process 346 and stored as DNA pool data comprising actual DNA-based storage 348 of the source binary data 342. The DNA string (nucleotide sequence) for the metadata and actual data remains the same, with the difference being that the metadata is stored in a blockchain 345 and the actual data is stored in a DNA pool (physical storage) 348. The metadata in the blockchain 345 is used to reference and access the actual data stored in the DNA storage 348. Any retrieval of data is performed by making a query to the blockchain for metadata stored pointing to the actual data stored in the DNA storage.

The cost involved for blockchain storage of the metadata is generally only a small fraction of the actual DNA based data storage technology. For example, storing 2 MB of digital data in DNA presently costs around $7000 for write operations and approximately $2000 for read operations. Some notable advantages of using a blockchain as metadata for DNA storage include data immutability in that once information is submitted to the blockchain it cannot be disrupted (i.e., blockchain is append-only storage; forever incremental), resistance to malicious Tampering (e.g., anti-ransomware) as even minor changes in the DNA sequence (single nucleotide) could have devastating implications, but data stored on the blockchain is immune from malicious tampering. The blockchain also provides decentralization and thus higher levels of security over centralized server stores. Currently, most data storage uses centralized system; furthermore, these systems are highly susceptible to attacks.

Thus, embodiments provide a new smart contract mechanism that helps create a new block in a blockchain only after performing deduplication at destination (DNA strings) and reduce the overall price of oligonucleotides synthesis. FIG. 3B illustrates a composition of digital data stored in blockchain metadata and DNA stored data, under some embodiments. As shown in FIG. 3B, the digital data 332 is stored as metadata 334 and data 336. The metadata is in a blockchain 338, which stores data that has been processed using LSH, key-value stores (KVS) and deduplication processes. The data 336 is stored in DNA pools within DNA storage 340.

Figure 4A:
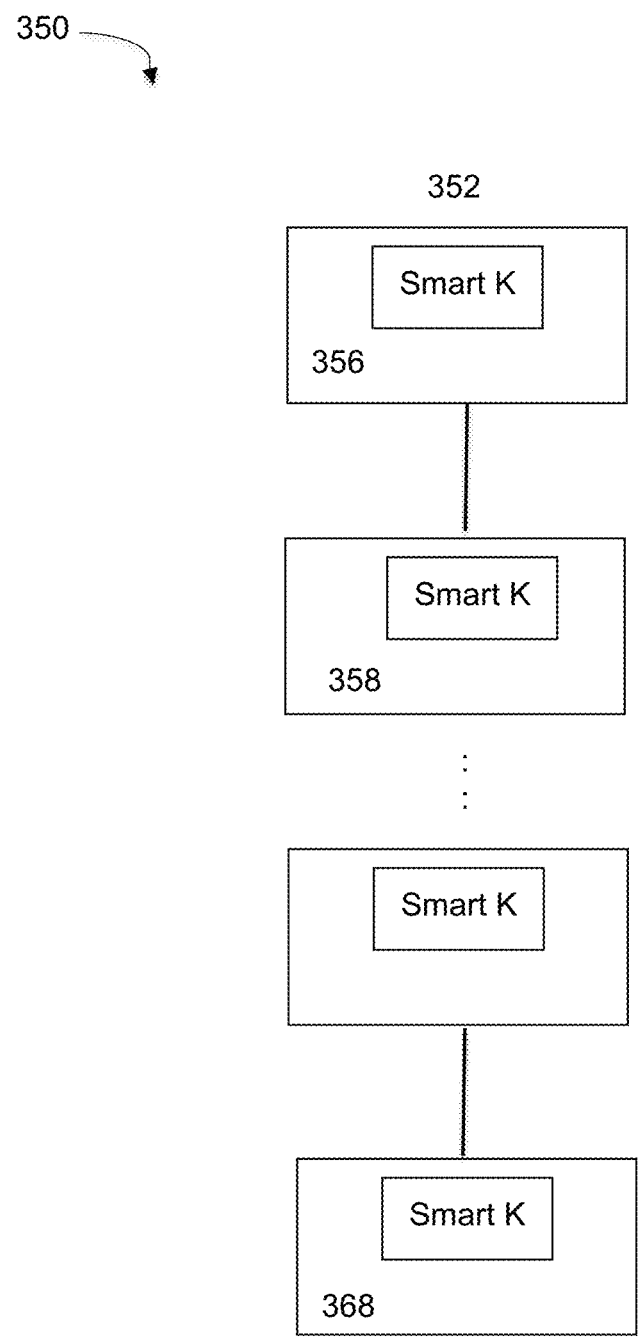
FIG. 4A is a diagram illustrating a general relationship of blockchain blocks and smart contracts, under some embodiments.

FIG. 4A is a diagram illustrating a general relationship of blockchain blocks and smart contracts, under some embodiments. As shown in diagram 350, a blockchain 352 comprises a number of blocks beginning with block 356 and ending with block 368. Any practical number of intermediate blocks (e.g., 358) may be included. The initial block 356 contains a smart contract ("Smart K") that is configured to help validate and generate a next block 358. In an embodiment, each block stores a data element representing data to be stored, where such data is typically generated using a deduplication backup process, such as 112 of FIG. 1. As new data is sent to be stored it is checked against a smart contract for storage as a new block, where each block size can be of a defined size or size range, such as on the order of 4 MB or less, although any other size is also possible. The block chain 352 thus forms a 'chain storage' of stored data that is validated by smart contracts and that is immutably stored on the blockchain. Depending on implementation, the smart contract may be implemented as a single smart contract or a respective smart contract associated with each block to generate a next block in the blockchain.

Figure 4B:
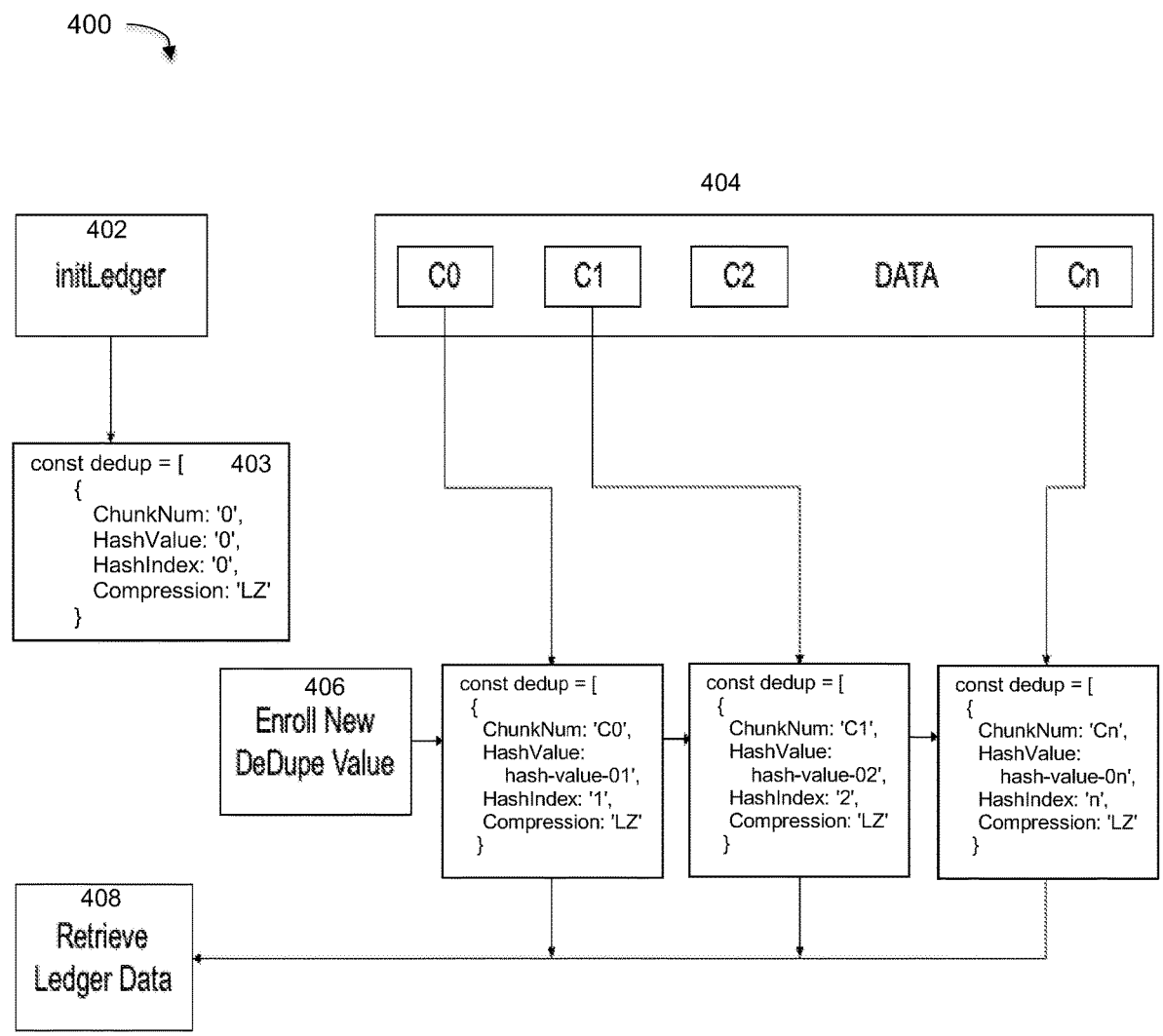
FIG. 4B is a combination block and flow diagram for implementing a smart contract for deduplication, under some embodiments.

FIG. 4B is a combination block and flow diagram for implementing a smart contract for deduplication, under some embodiments. Process 400 of FIG. 4B illustrates operation of the similarity-based deduplication process 304 of FIG. 3A in an embodiment. As shown in the example embodiment of FIG. 4B, a genetic data in the form of a DNA sequence for a source data file of a certain size (e.g., a 2 GB file) comprises a sequence of strings (e.g., AGTTCA . . . ). This sequence data is chunked into chunks 404 of a certain size (e.g., <=4 MB). Each chunk of data (C0, C1, C2, . . . Cn) is output to be stored in the blockchain. For this embodiment, actual biological DNA is not stored on the blockchain, but genetic data (AGTTCA . . . ) in the form of a binary file (e.g., BAM file) is stored on the blockchain. Thus, DNA sequence data comprising metadata The blockchain stores database data in the form of key-value pairs. Initially when the system loads a smart contract, the initial value of these key-value; pairs is assigned. In the database these values are managed using put and push methods. As shown in diagram 400, the initial ledger (IniLedger) 402 comprises the data structure 403:

```
const dedup = [
  {
    ChunkNum: '0',
    HashValue: '0'
    HashIndex: '0',
    Compression: 'LZ'
  },
```

When the initial ledger 402 is started, the smart contract calls a put method, which will initialize the ledger with NULL values. EnrollNewDedupValues: As a file stream arrives to the deduplication system (e.g., Data Domain), the data 404 is divided into chunks, denoted C0, C1 to Cn. An enroll new deduplication values (EnrollNewDedupValues) process 406 captures the ChunkNum, HashValue, HashIndex and Compression values for each of the data chunks, Cx. These values will call a put method in the smart contract to push the data to a ledger database. For example:

```
const dedup = [
  {
    ChunkNum: 'C1',
    HashValue: '0x329474ssad',
    HashIndex: '1',
    Compression: 'LZ'
  }
  Updated ledger value.
```

With respect to retrieving the ledger data, reconstruction of the actual ledger transaction is required to recreate the file. In that moment, a push smart contract function is used. The user can provide the chunk number (ChunkNum, Cx) as input to the smart contract function to get the block (chunk) information.

Figure 5:
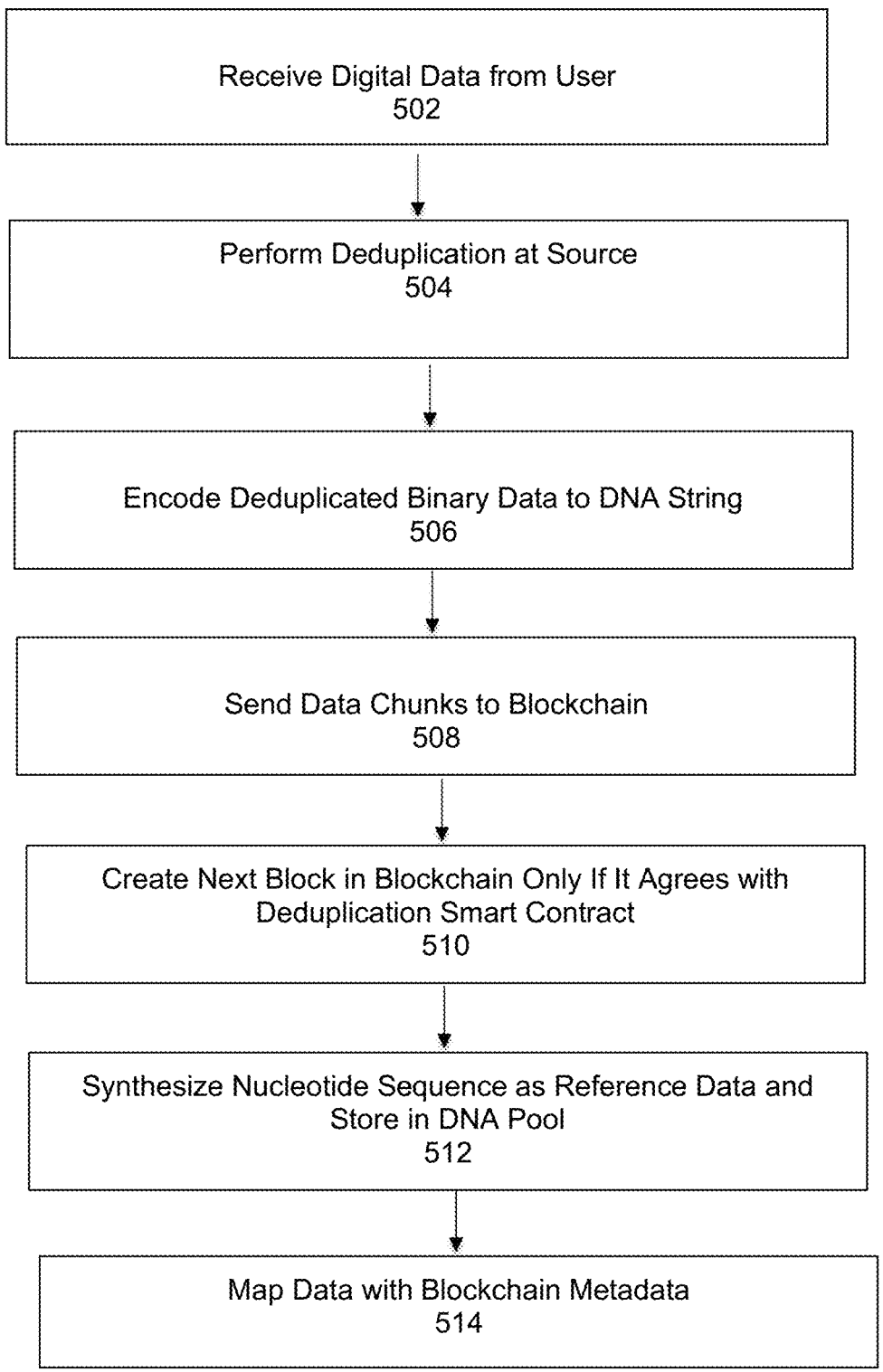
FIG. 5 is a flowchart illustrating a method of storing digital data in DNA using a blockchain for DNA sequences deduplicated at the destination site, under some embodiments.

FIG. 5 is a flowchart illustrating a method of storing digital data in DNA using a blockchain for DNA sequences deduplicated at the destination site, under some embodiments. The process of FIG. 5 can be performed for one or any number of users depending on the system configuration. FIG. 5 illustrates a process for a storage (write) path, and begins with the system receiving digital data from a user, 502. The source site deduplicates this data using deduplication process, such as Data Domain, 504. The system then encodes this deduplicated binary data to a DNA string, 506. The chunk size may be defined as any appropriate size, such as data chunk size <4 MB. Each data chunk is then sent to the blockchain network, 508. The next block in the blockchain is only created if it agrees with the deduplication smart contract, 510. All the deduplicated data (DNA sequence) is stored in the blockchain as "reference data." The oligonucleotide sequence of this reference data is synthesized as actual DNA strings and stored in the DNA pool. The data is also mapped with the appropriate blockchain metadata, 514.

Figure 6:
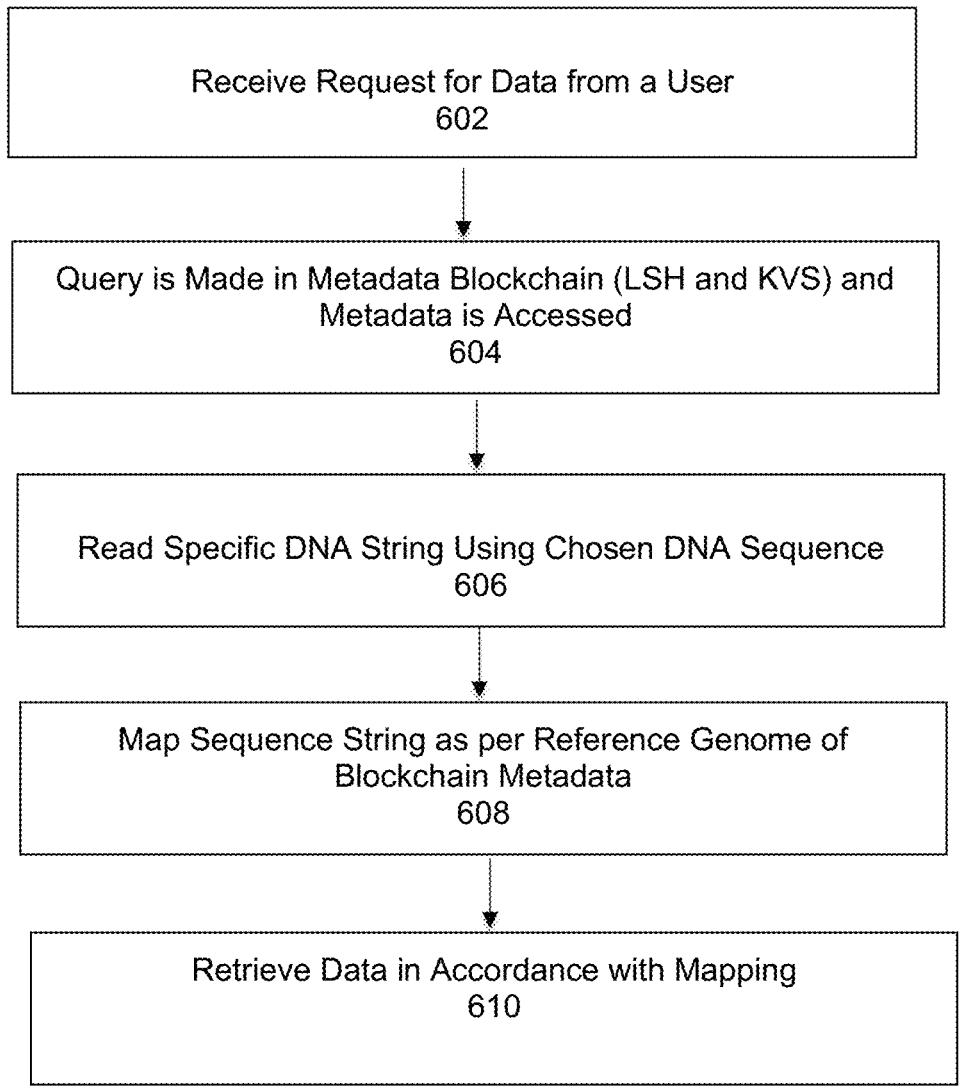
FIG. 6 is a flowchart illustrating a method of reading digital data in DNA using a blockchain for DNA sequences deduplicated at the destination site, under some embodiments.

FIG. 6 is a flowchart illustrating a method of reading digital data in DNA using a blockchain for DNA sequences deduplicated at the destination site, under some embodiments. FIG. 6 illustrates a process for a retrieval (read) path, and begins with the system receiving a user request for data, 602. A query (random read) is then made in the blockchain LSH and KVS and the metadata is accessed, 604. The specific DNA string is read using a DNA sequence of choice, 606. The DNA sequence string is mapped in accordance with the "reference genome" of the blockchain metadata, 608, and the data is then retrieved (read), 610.

Figure 7:
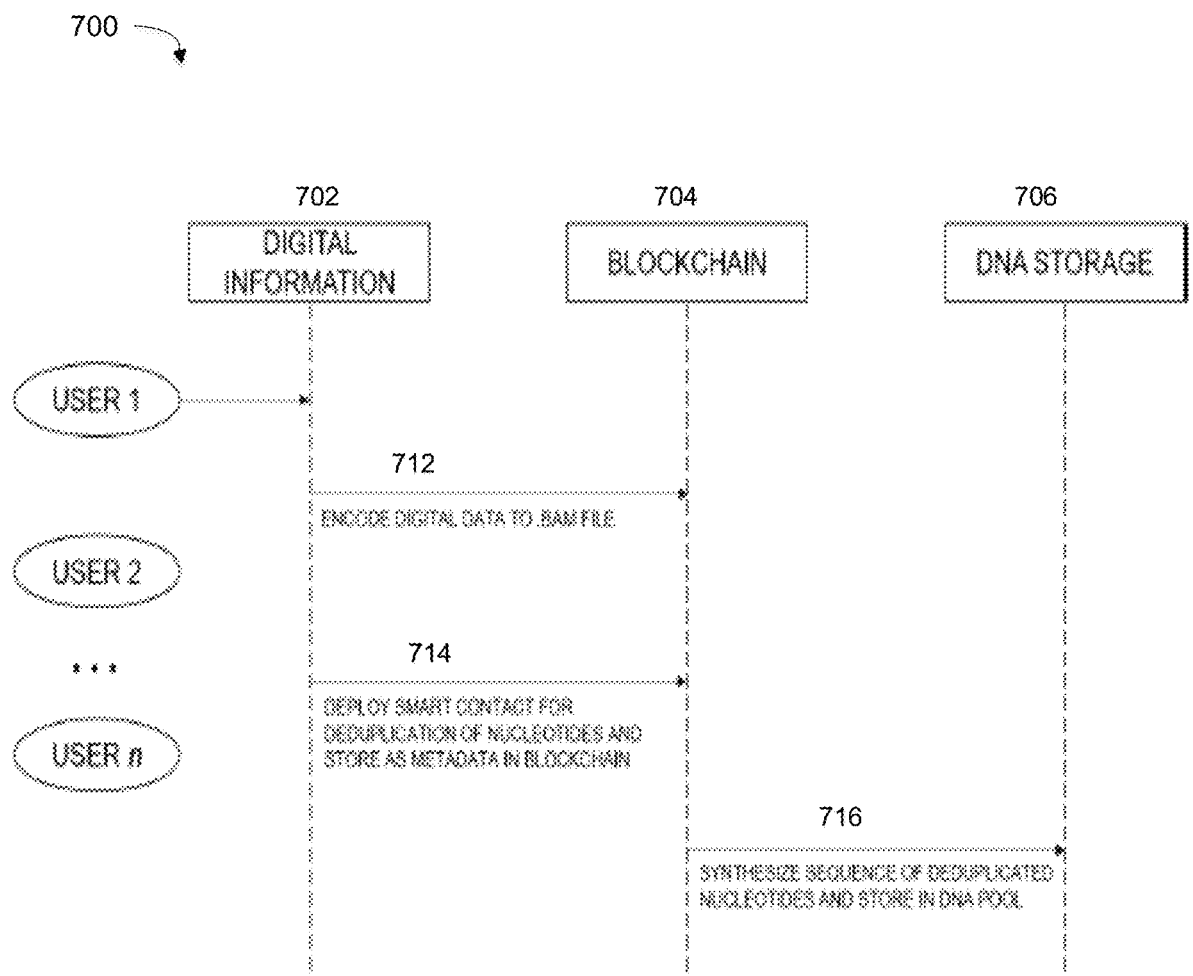
FIG. 7 is a sequence diagram illustrating storage of digital data in DNA storage using a blockchain, under some embodiments.

FIG. 7 is a sequence diagram illustrating storage of digital data in DNA storage using a blockchain, under some embodiments. As shown in diagram 700, a number of users (1 to n) can generate digital data 702. Digital data for a specific user is encoded to an appropriate format, such as a .BAM file or similar and written to blockchain 704. A .BAM (Binary Aligned Map) file is a binary version of a SAM file, which is a tab-delimited text file that contains sequence alignment data. Any similar or other appropriate file format may also be used. Process 700 also deploys a smart contract for deduplication of nucleotides and stores this as metadata in the blockchain 704. The deduplicated nucleotides is synthesized and then stored in DNA pools in DNA storage 706.

As shown in FIG. 7, the main process steps are encoding 712 the digital data to an appropriate format (e.g., .BAM file) for storage on blockchain 712; deploying a smart contract for deduplication and metadata storage, 714, and synthesizing the deduplicated nucleotides for storage in DNA storage, 716. Example details for each of these main processes will be provided below.

Figure 8:
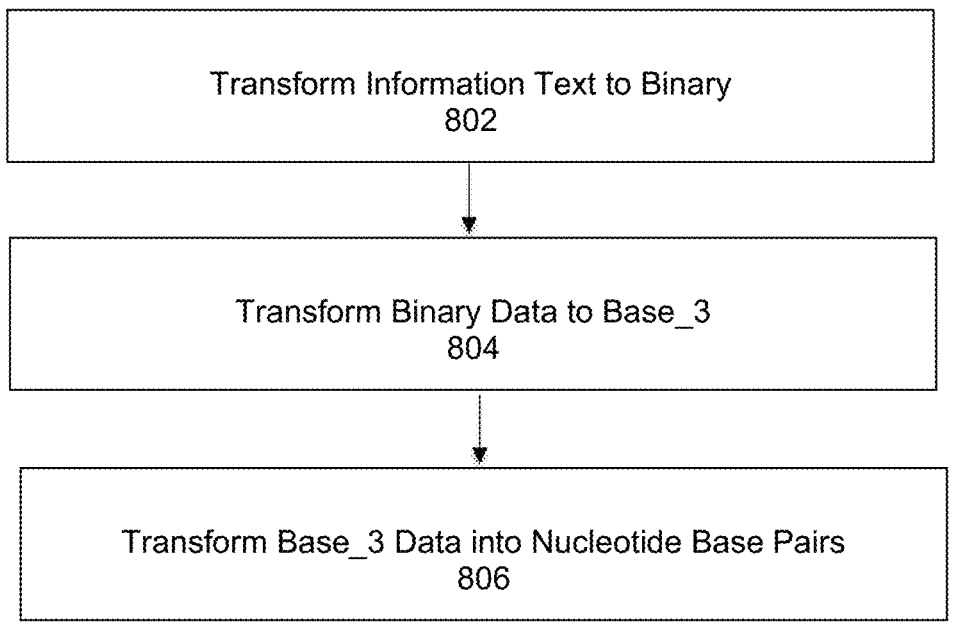
FIG. 8 is a flowchart illustrating an overall process of encoding digital data to a DNA sequence, under some embodiments.

With respect the encoding step 712, FIG. 8 is a flowchart illustrating an overall process of encoding digital data to a DNA sequence, under some embodiments. The first step 802 is to transform the text of the data into binary format. For example, to store the text "Dell Technologies" for storage in DNA, it is first transformed to binary format, so this becomes:

01000100 01100101 01101100 01101100 00100000 01010100 01100101 01100011 01101000 01101110 01101111 01101100 01101111 01100111 01101001 01100101 01110011.

The binary (Base_2) data is then transformed into Base_3 format, 804. Thus, for the example above, the binary data becomes in Base_3:

2122 10202 11000 11000 1012 10010 10202 10200 10212 11002 11010 11000 11010 10211 10220 10202 11021.

The Base_3 data is then transformed into to nucleotide base pairs, 806. This conversion can be done using a table, such as using Table 2 below:

TABLE 2

| Previous | Next triplet To Encode | | |
|---|---|---|---|
| nucleotide | 0 | 1 | 2 |
| A | C | G | T |
| C | G | T | A |
| G | T | A | C |
| T | A | C | G |

For the example above, the Base_3 data becomes base pair data:

TCAT GTGTG GACGT GACGT GTCA GTAGT GTGTG GTGTA GTGAT GACG GACTA GACGT GACTA GTGAG GTGCG GTGTG GACAG.

This sequence thus represents the text "Dell Technologies" as an nucleotide string.

Following is example program code to execute a process of encoding digital information to a DNA sequence. This code is provided for purposes of example only, and embodiments are not so limited. Any similar or other program code may be used.

```
buildBAM.py
encoded DNA strings in a .bam file
Usage: $ python buildBAM.py
import pysam
# Customized Fields
    header = { 'HD': {'VN': '1.0'},
        'SQ': [{'LN': 1575, 'SN': 'chr1'},
            {'LN': 1584, 'SN': 'chr2'}] }
# output file
tmpfilename = 'encode_dna.bam'
with pysam.AlignmentFile(tmpfilename, "wb", header=header) as outf:
    a = pysam.AlignedSegment()
    a.query_name = "read_28833_29006_6945"
# String to be encoded
    a.query_sequence= "TCATGTGTGGACGTGACGTGTCAGTAGTGTGTGGT"
    a.query_sequence= "GTAGTGATGACGGACTAGACGTGACTAGTGAGGTG"
    a.query_sequence= "GTGAGGTGCGGTGGCATGCTGGACCTAGTGAGGTG"
    a.flag = 99
    a.reference_id = 0
    a.reference_start = 32
    a.mapping_quality = 20
    a.cigar = ((0,10), (2,1), (0,25))
    a.next_reference_id = 0
    a.next_reference_start=199
```

```
    a.template_length=167
    a.query_qualities =
pysam.qualitystring_to_array("<<<<<<<<<<<<<<<<<<<<:<9/,&,22;;<<<")
    a.tags = (("NM", 1),
        ("RG", "L1"))
    outf.write(a)
```

As shown in FIG. 7, a second main process step 714 is storing the DNA sequence in a blockchain. Following is example program code to execute a process of this blockchain storage process. This code is provided for purposes of example only, and embodiments are not so limited. Any similar or other program code may be used.

```
[root@user-10 ]# python data_blockchain.py encode_data.bam -cn dna
-dr
blockchain
--CHAIN CREATION--
Created chain
MultiChain 2.0.6 Daemon (latest protocol 10012)
Starting up node...
Looking for genesis block...
Genesis block found
Other nodes can connect to this node using:
multichaind dna@10.230.163.210:6809
This host has multiple IP addresses, so from some networks:
multichaind dna@192.168.122.1:6809
Listening for API requests on port 6808 (local only - see rpcallowip
setting)
Node ready.
--STREAM CREATION--
--PREPROCESSING--
--INSERTING DATA--
Chain construction complete! Chain name: dna
Total memory in bytes:
14921728
[root@dell-10 ]# ls -ltr blockchain/dna/
total 2084
-rw-r--r-- 1 root root 8473 May 28 05:47 params.dat.bak
-rw-r--r-- 1 root root 79 May 28 05:47 multichain.conf
drwxr-xr-x 2 root root 85 May 28 05:47 permissions.db
-rw------- 1 root root 5 May 28 05:47 multichain.pid
-rw------- 1 root root 0 May 28 05:47 db.log
drwx------ 2 root root 28 May 28 05:47 database
-rw------- 1 root root 8705 May 28 05:48 params.dat
drwx------ 2 root root 85 May 28 05:48 entities.db
drwx------ 2 root root 85 May 28 05:48 chainstate
drwx------ 3 root root 59 May 28 05:48 blocks
-rw------- 1 root root 16384 May 28 05:48 wallet.dat
-rw------- 1 root root 307072 May 28 05:56 permissions.dat
-rw-r--r-- 1 root root 638433 May 28 05:56 permissions.log
-rw------- 1 root root 111264 May 28 05:56 entities.dat
drwx------ 3 root root 4096 May 28 05:56 wallet
-rw------- 1 root root 255187 May 28 05:56 debug.log
```

As shown in FIG. 7, a third main process step 714 is deploying a smart contract for deduplication and storage of metadata. Each new incoming data will be added to a new block of blockchain based on the smart contact which will deploy the logic of deduplication. In general, this process involves processing millions of small text files (DNA Sequences) and creating hash of these large number of files. The comparison operations are thus a performance and time bottleneck. Existing approaches like identify-based deduplication have their known disadvantages when dealing with this problem. For example, file-based deduplication is generally not effective as the process will return mostly unique sequences, block-based duplication (e.g., Rabin fingerprinting) does not yield much redundant data as distribution of sequences varies from each incoming nucleotide sequence, and application-aware deduplication using file structure and content does not help as metadata fields will mostly be unique.

Figure 9:
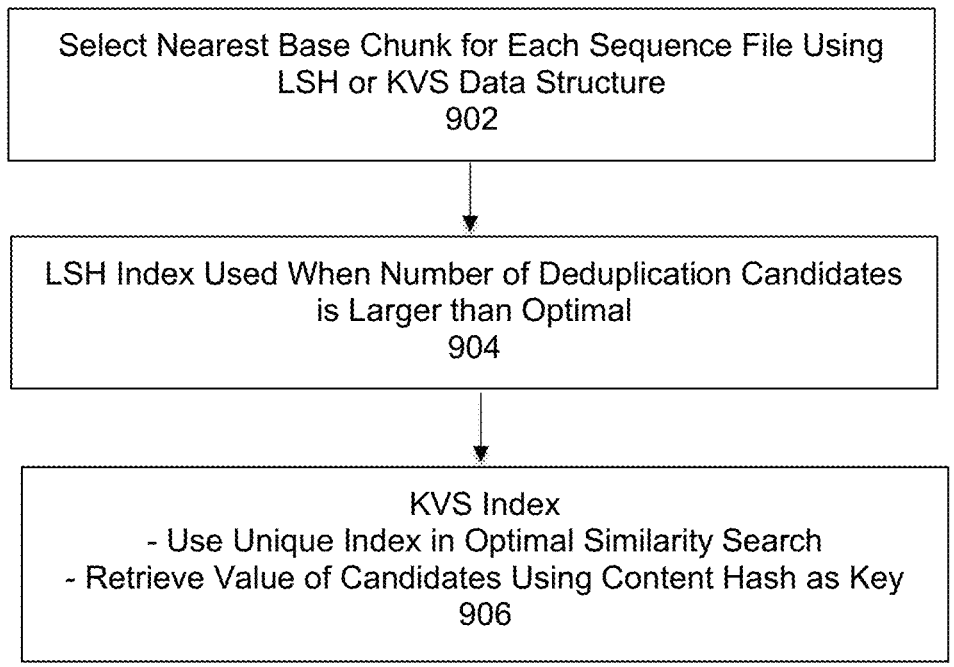
FIG. 9 is a flowchart illustrating a method of performing similarity-based deduplication, under some embodiments.

Embodiments use a hybrid approach of similarity-based deduplication since the data set involves genomic text data, with delta-encoding. This approach provides at least two advantages: first, it stores together a pointer to the most similar entry; and second, for a read operation a minimal list of modification is required for an original object from a current entry. FIG. 9 is a flowchart illustrating a method of performing similarity-based deduplication, under some embodiments. The first step 902 of the similarity-based deduplication process is to select the nearest base chunk for each sequence in .bam file using a selected data structure of either LSH or KVS. Using a Locality-Sensitive Hashing (LSH) index 904 enables a similarity search when the number of deduplication candidates is too large to efficient perform optimal searches, where a determination of efficient performance can be defined using defined thresholds for acceptable performance standards in a given deployment environment. For Key-value store (KVS) indexing, 906, the process uses unique entries in an optimal similarity search, and retrieves the value of candidates (deduplication) using their content hashes as keys. Generally, KVS is tried first and then LSH is used if there are too many candidates for efficient processing. A data storage component is used to store the new block of blockchain, and this is used for creating/re-creating (synthesizing) the sequence of nucleotides.

Figure 10:
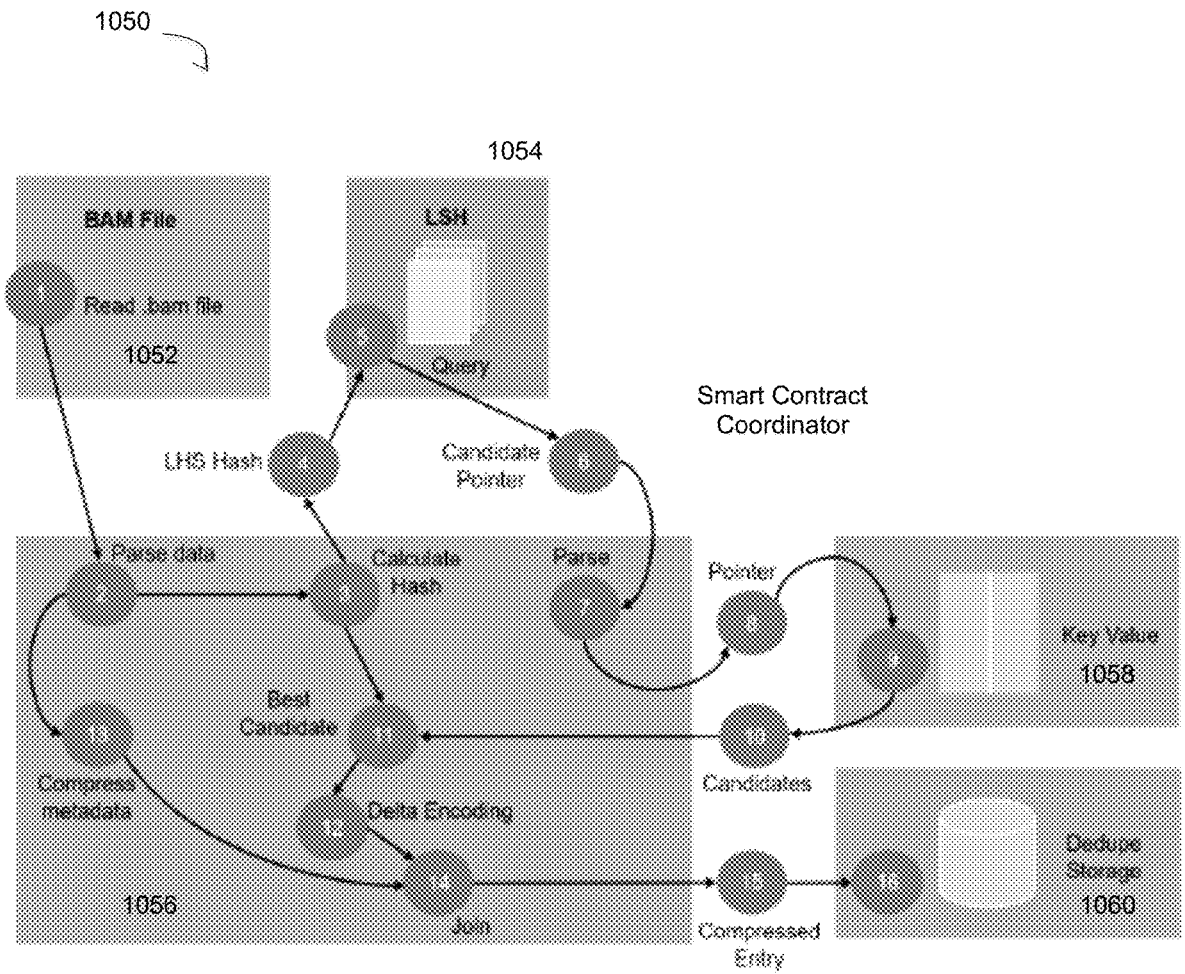
FIG. 10 is a combination block and flow diagram of a system and process for implementing a deduplication smart contract, under some embodiments.

FIG. 10 is a combination block and flow diagram of a system and process for implementing a deduplication smart contract, under some embodiments. FIG. 10 illustrates some functional components used in a method of deduplicating nucleotides and storing them as metadata on a blockchain.

As shown in FIG. 10, diagram 1050 shows DNA data 1052 in the form of a .BAM file, a deduplication engine (processing unit) 1054, LSH 1056, a Key Value store 1058, and deduplication storage 1060. The process of FIG. 10 proceeds by (1) first reading input digital information transformed as nucleotides sequence in a .BAM file. This .BAM file is input to similarity-based deduplication engine 1056 and the process parses it (2) to calculate a hash value (3) and compress the metadata (13). The parsed data is nucleotide sequence for which the hash value (4) is calculated and which is sent to the LSH (Locality Sensitive Hashing) component 1054. The process then obtains the internal LSH key from these hashes (5). It does this by using a query respective LSH Hash index, and joining the list of pointers to candidates in a bigger list. The candidate pointer (6) is then returned to the deduplication component. Component 1056 receives a list of pointers to the candidate pointer (7). It then sends this pointer (8) to KVS 1058. The KVS obtains the candidate value using each pointer as a key (9), and returns a list of candidates (10). The deduplication engine 1056 calculates an edit distance between each candidate from received list (11). For this, an edit operation to delta encoding (e.g., Huffman encoding) is performed (12). The metadata is compressed (e.g., .BAM file header) (13), and this compressed metadata is joined with the delta encoded data (14) to form a compressed entry (15). This reduced (compressed) data is then sent to deduplication storage 1060 and written as entry to a new blockchain block. FIG. 10 illustrates functional components of logic to implement and execute a smart contract, and may be referred to as a smart contract coordinator component comprising the deduplication component 1056, and the LSH and KVS processes, among other processes.

FIG. 10 illustrates a sequence of steps that constitute a write operation. These process steps can be reversed to perform a read operation.

Figure 11A:
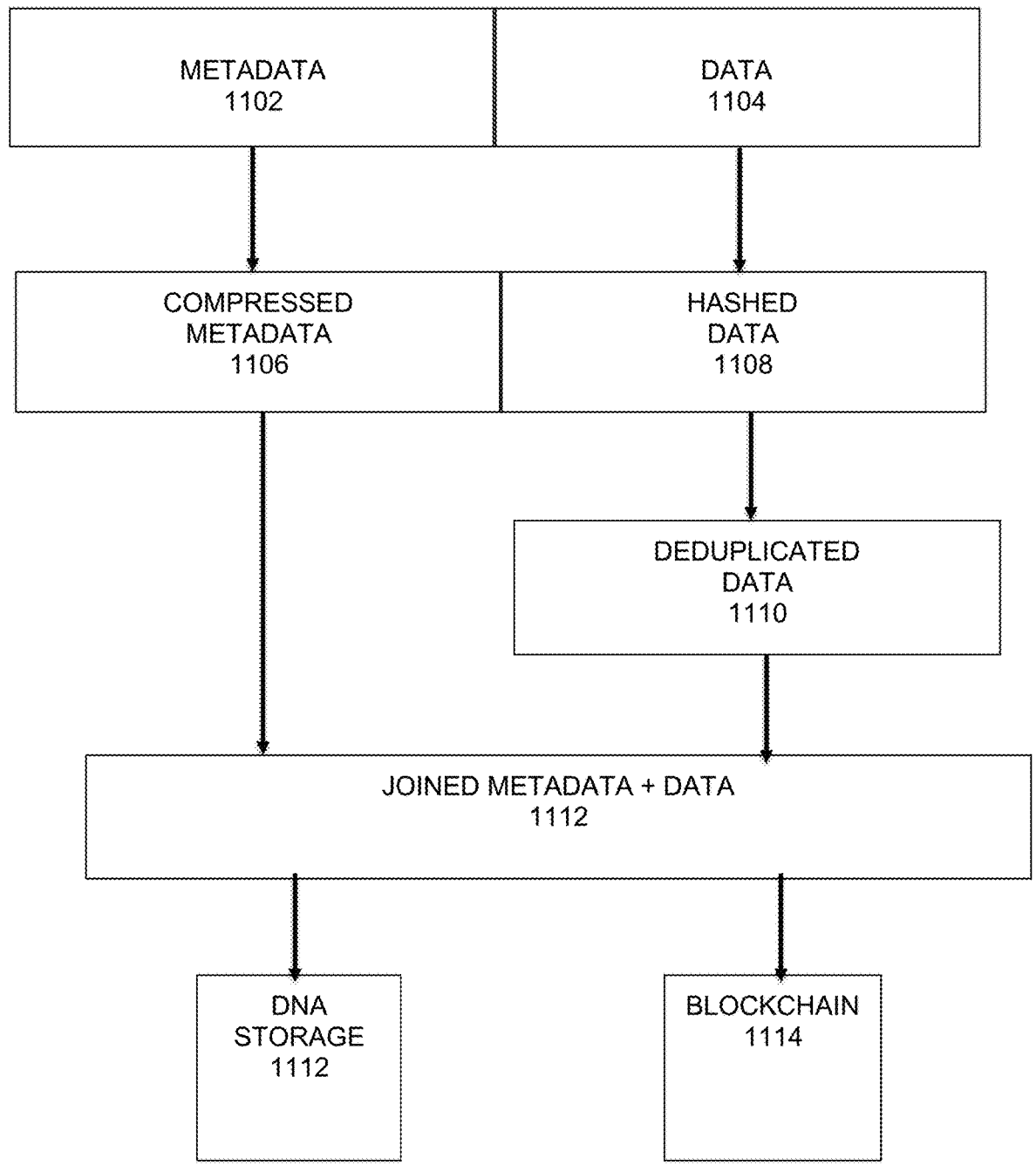
FIG. 11A illustrates the processing of metadata and data in the system of FIG. 10, under some embodiments.

FIG. 11A illustrates the generation and processing of different aspects of the metadata and data as they are processed in system 1050. As shown in FIG. 11, metadata 1102 is compressed to form compressed metadata 1106. The data 1104 is hashed to produce hashed data 1108. This data is then deduplicated using the smart contract process described above to form deduplicated data 1110 (such as shown in diagram 1050 of FIG. 10). The deduplicated data is then joined 1112 with the compressed metadata, and this joined data is stored in DNA storage 1112 and written to the blockchain 1114 if the smart contract is valid.

Figure 11B:
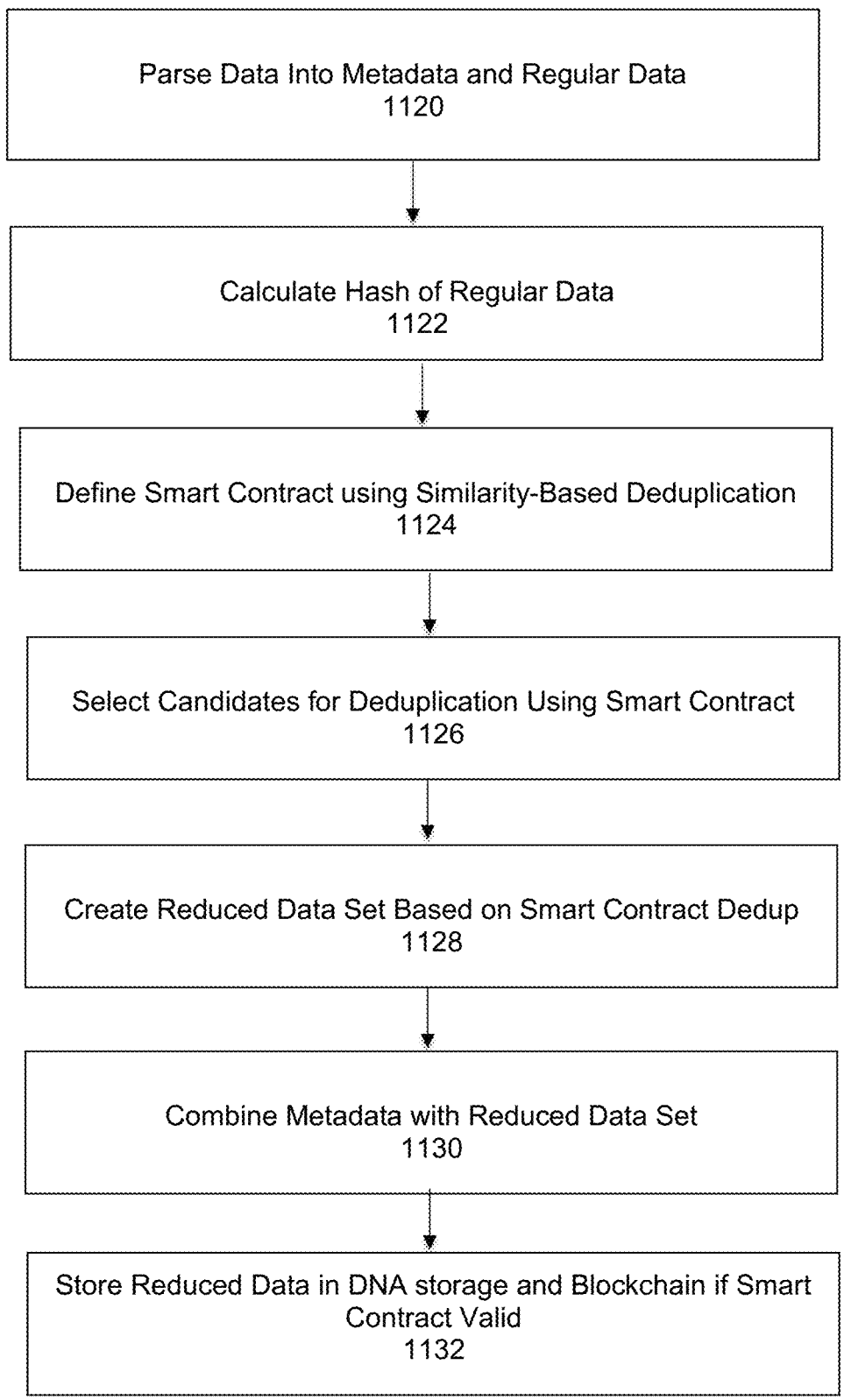
FIG. 11B is a flowchart illustrating an overall process of generating and storing the metadata and data of FIG. 11A, under some embodiments.

FIG. 11B is a flowchart illustrating an overall process of generating and storing the metadata and data of FIG. 11A in blockchain storage, under some embodiments. The process of FIG. 11B starts by parsing the input data into metadata and regular data, 1120. The hash of the regular data is then calculated, 1122. A smart contract is defined using similarity-based deduplication, 1124. Candidates for destination-side deduplication are then selected using the smart contract, 1126. This creates a reduced dataset based on smart contract deduplication, 1128. The metadata (which may be compressed) is combined with the reduced data, 1130, and this combined data is then stored in DNA storage and written to the blockchain if the smart contract is valid, 1132.

Although embodiments are described with respect to storage of metadata on a blockchain using the binary to trinary to nucleotide base pairs for deduplication, embodiments are not so limited. Besides deduplication, applications may encompass many other purposes for storing data in DNA storage. For these embodiments, the similarity-based deduplication process on the destination side may be omitted, and the process would encompass storing genetic (DNA sequence) data on the blockchain for any source data (e.g., non-Data Domain) system.

As stated previously, DNA storage provides several valuable advantages, such as immutability and decentralization. With respect to immutability, as even minor changes in the DNA sequence (single nucleotide) could have devastating implications (Carrier Vs. Non-Carrier) the data stored on the blockchain is immune from malicious tampering and will be kept for a very long periods of time. The decentralization of the genetic data provides higher levels of security over centralized server storages. By deploying consensus mechanisms and data sharing embodiments can be used to create very secure systems for storing and sharing genomic data.

Embodiments can help provide collaboration across various organizations through proof of ownership mechanisms. For example, proof of ownership for genetic data can be used by an organization to support a claim that that they were the first to perform sequencing of specific DNA. The blockchain could be implemented as either a public chain or a private chain depending on use case. For example, a public chain could be used for users to store, share and participate in genetic services/research. An example use of a private blockchain would be for health organizations providing genetic services for patients, where it is beneficial for such organizations to have their data stored over decentralized systems such as provided by private chains. One of the major driving forces for the success of a dedicated genetic blockchain is the participation of the users in genetic research, where they can share data anonymously with Pharma companies and research institutes. For this scenario, users will need to share their DNA sequence and genetic data. Since a blockchain is the preferred manner for data sharing in terms of security and privacy, such sequences can be stored on a specially dedicated blockchain and then shared in a controlled manner by the users rather than users uploading their sequences from centralized servers and then sharing it on a public blockchain. Embodiments of the DNA data storage system and blockchain implementation using smart contract deduplication processes can help achieve these solutions.

System Implementation

Figure 12:
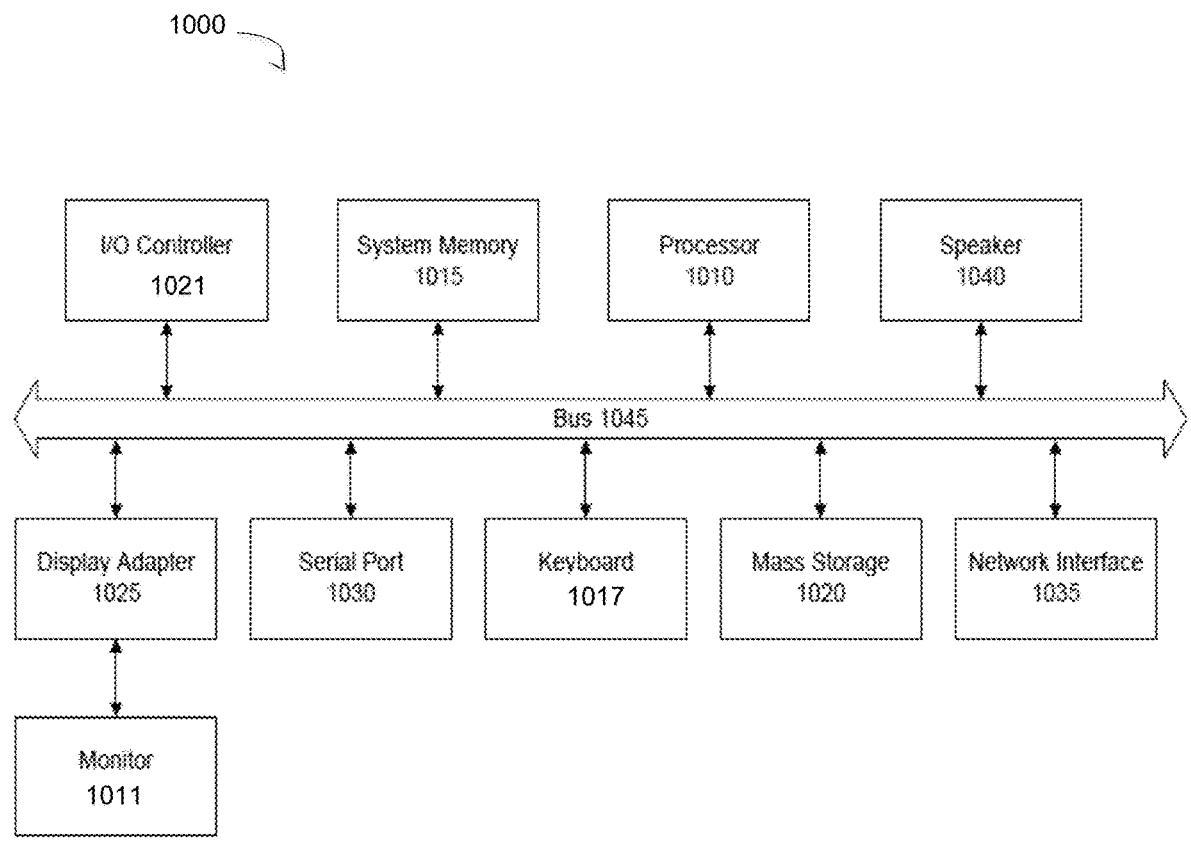
FIG. 12 is a block diagram of a computer system used to execute one or more software components of a deduplication system for DNA storage, under some embodiments.

As described above, in an embodiment, system 100 includes a DNA storage support process 121 that may be implemented as a computer implemented software process, or as a hardware component, or both. As such, it may be an executable module executed by the one or more computers in the network, or it may be embodied as a hardware component or circuit provided in the system. The network environment of FIG. 2 may comprise any number of individual client-server networks coupled over the Internet or similar large-scale network or portion thereof. Each node in the nets work(s) comprises a computing device capable of executing software code to perform the processing steps described herein. FIG. 12 is a block diagram of a computer system used to execute one or more software components of described herein. The computer system 1000 includes a monitor 1011, keyboard 1017, and mass storage devices 1020. Computer system 1000 further includes subsystems such as central processor 1010, system memory 1015, input/output (I/O) controller 1021, display adapter 1025, serial or universal serial bus (USB) port 1030, network interface 1035, and speaker 1040. The system may also be used with computer systems with additional or fewer subsystems. For example, a computer system could include more than one processor 1010 (i.e., a multiprocessor system) or a system may include a cache memory.

Arrows such as 1045 represent the system bus architecture of computer system 1000. However, these arrows are illustrative of any interconnection scheme serving to link the subsystems. For example, speaker 1040 could be connected to the other subsystems through a port or have an internal direct connection to central processor 1010. The processor may include multiple processors or a multicore processor, which may permit parallel processing of information. Computer system 1000 is an example of a computer system suitable for use with the present system. Other configurations of subsystems suitable for use with the present invention will be readily apparent to one of ordinary skill in the art.

Computer software products may be written in any of various suitable programming languages. The computer software product may be an independent application with data input and data display modules. Alternatively, the computer software products may be classes that may be instantiated as distributed objects. The computer software products may also be component software. An operating system for the system may be one of the Microsoft Windows®. family of systems (e.g., Windows Server), Linux, Mac OS X, IRIX32, or IRIX64. Other operating systems may be used. Microsoft Windows is a trademark of Microsoft Corporation.

Although certain embodiments have been described and illustrated with respect to certain example network topographies and node names and configurations, it should be understood that embodiments are not so limited, and any practical network topography is possible, and node names and configurations may be used. Likewise, certain specific programming syntax and data structures are provided herein. Such examples are intended to be for illustration only, and embodiments are not so limited. Any appropriate alternative language or programming convention may be used by those of ordinary skill in the art to achieve the functionality described.

Embodiments may be applied to data, storage, industrial networks, and the like, in any scale of physical, virtual or hybrid physical/virtual network, such as a very large-scale wide area network (WAN), metropolitan area network (MAN), or cloud based network system, however, those skilled in the art will appreciate that embodiments are not limited thereto, and may include smaller-scale networks, such as LANs (local area networks). Thus, aspects of the one or more embodiments described herein may be implemented on one or more computers executing software instructions, and the computers may be networked in a client-server arrangement or similar distributed computer network. The network may comprise any number of server and client computers and storage devices, along with virtual data centers (vCenters) including multiple virtual machines. The network provides connectivity to the various systems, components, and resources, and may be implemented using protocols such as Transmission Control Protocol (TCP) and/or Internet Protocol (IP), well known in the relevant arts. In a distributed network environment, the network may represent a cloud-based network environment in which applications, servers and data are maintained and provided through a centralized cloud-computing platform.

For the sake of clarity, the processes and methods herein have been illustrated with a specific flow, but it should be understood that other sequences may be possible and that some may be performed in parallel, without departing from the spirit of the invention. Additionally, steps may be subdivided or combined. As disclosed herein, software written in accordance with the present invention may be stored in some form of computer-readable medium, such as memory or CD-ROM, or transmitted over a network, and executed by a processor. More than one computer may be used, such as by using multiple computers in a parallel or load-sharing arrangement or distributing tasks across multiple computers such that, as a whole, they perform the functions of the components identified herein; i.e., they take the place of a single computer. Various functions described above may be performed by a single process or groups of processes, on a single computer or distributed over several computers. Processes may invoke other processes to handle certain tasks. A single storage device may be used, or several may be used to take the place of a single storage device.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

All references cited herein are intended to be incorporated by reference. While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of storing digital data in DNA storage comprising:

deploying a backup server running a deduplication backup program for deduplicating and backing up digital data;

receiving input file data comprising text information as part of the digital data to be backed up;

encoding the input file data into an oligonucleotide sequence to produce sequence data through a transformation of text to binary to Base_3 encoding;

organizing the Base_3 sequence data into chunks of a defined chunk size;

applying one or more similarity-based deduplication routines of the deduplication backup program including using key/value pairs for locality similarity hashing (LSH) to reduce a number of nucleotides for data representation;

defining a smart contract stored persistently in a blockchain for the oligonucleotide sequence for the deduplication backup program using variable length, specific-to-triplet codons to provide improved read performance compared to compression;

storing the deduplicated chunks in a block of the blockchain only if the block agrees with the smart contract, wherein the smart contract creates a new block in the blockchain only after deduplication at a storage target.

2. The method of claim 1 wherein the oligonucleotide sequence comprises base pairs of adenine (A), cytosine (C), guanine (G) and thymine (T) nucleotides.

3. The method of claim 2 wherein the oligonucleotide sequence comprises metadata for the input file data that refers to actual data stored in the DNA storage.

4. The method of claim 3 wherein the actual data comprises data formed by synthesizing the oligonucleotide sequence in a DNA synthesis process, and wherein the DNA storage comprises a DNA pool for storage of synthesized genetic data as the actual data.

5. The method of claim 1 wherein new data to be stored is checked against the smart contract to validate a next data block stored on the blockchain.

6. The method of claim 1 wherein the blockchain is one of a public blockchain or a private blockchain, the method further comprising:

initially loading the defined smart contract with an initial key-value pair managed using put and push methods;

receiving a file stream with new data;

dividing the new data into data chunks;

pushing the new data to a ledger database using a put method in the smart contract; and using, for retrieval of the new data, a smart contract push function to retrieve a respective data chunk.

7. The method of claim 1 wherein the oligonucleotide sequence is formatted into a binary array map (BAM) file format.

8. The method of claim 1 wherein the backup server comprises part of a restorer-based deduplication storage system, and further uses variable length deduplication with delta encoding at the storage target storing the digital data.

9. The method of claim 1 wherein the data comprises classified data that is intended to be kept in secure storage.

10. A system for storing digital data in DNA storage comprising:
   an interface receiving input file data comprising text information of the digital data;
   a backup server running a deduplication backup program for deduplicating and backing up the digital data;
   a first processing system encoding the input file data into an oligonucleotide sequence to produce sequence data through a transformation of text to binary to Base_3 encoding, and organizing the Base_3 sequence data into chunks of a defined chunk size; and
   a similarity-based deduplication backup processing system of the backup server using key/value pairs for locality similarity hashing (LSH) to reduce a number of nucleotides for data representation;
   a smart contract processing system defining a smart contract stored persistently in a blockchain for the oligonucleotide sequence for the deduplication backup program using variable length, specific-to-triplet codons to provide improved read performance compared to compression; and
   system memory storing the deduplicated chunks in a block of the blockchain only if the block agrees with the smart contract, wherein the smart contract creates a new block in the blockchain only after deduplication at a storage target.

11. The system of claim 10 wherein the oligonucleotide sequence comprises base pairs of adenine (A), cytosine (C), guanine (G) and thymine (T) nucleotides, and wherein the oligonucleotide sequence is formatted into a binary array map (BAM) file format.

12. The system of claim 11 wherein the oligonucleotide sequence comprises metadata for the input file data that refers to actual data stored in the DNA storage, and wherein the actual data comprises data formed by synthesizing the oligonucleotide sequence in a DNA synthesis process, and wherein the DNA storage comprises a DNA pool for storage of synthesized genetic data as the actual data.

13. The system of claim 12 wherein new data to be stored is checked against the smart contract to validate a next data block stored on the blockchain.

14. The system of claim 10 wherein the blockchain is one of a public blockchain or a private blockchain, and wherein the data comprises classified data that is intended to be kept in secure storage, and further wherein the backup server comprises part of a restorer-based deduplication storage system, and uses variable length deduplication with delta encoding at the storage target storing the digital data, the method further comprising:
   initially loading the defined smart contract with an initial key-value pair managed using put and push methods;
   receiving a file stream with new data;
   dividing the new data into data chunks;
   pushing the new data to a ledger database using a put method in the smart contract; and
   using, for retrieval of the new data, a smart contract push function to retrieve a respective data chunk.

15. A method of storing digital data in DNA storage comprising:
   receiving deduplicated input file generated by a backup system executing a deduplication backup process;
   deploying a backup server running a deduplication backup program for deduplicating and backing up digital data to receive an input file for the digital data;
   encoding the input file data into an oligonucleotide sequence;
   dividing oligonucleotide sequence data into chunks of a defined chunk size;
   applying one or more similarity-based deduplication routines of the deduplication backup program including using key/value pairs for locality similarity hashing (LSH) to reduce a number of nucleotides for data representation;
   defining a smart contract stored persistently in a blockchain for the oligonucleotide sequence for the deduplication backup program using variable length, specific-to-triplet codons to provide improved read performance compared to compression; and
   storing the deduplicated chunks in a block of a blockchain as metadata referencing actual data of the input file stored as a DNA synthesized version of the oligonucleotide sequence, and only if the block agrees with the smart contract, wherein the smart contract creates a new block in the blockchain only after deduplication at a storage target.

16. The method of claim 15 wherein new data to be stored is checked against the smart contract to validate a next data block stored on the blockchain.

17. The method of claim 16 wherein the input file data comprises one of text data, image data, or file data produced by an application executed on a client computer of the backup system, and wherein the oligonucleotide sequence comprises base pairs of adenine (A), cytosine (C), guanine (G) and thymine (T) nucleotides.

18. The method of claim 17 further comprising producing the oligonucleotide sequence data through a transformation of input file data to binary to Base_3 encoding.

19. The method of claim 18 wherein the data comprises classified data that is intended to be kept in secure storage, and the DNA storage comprises DNA storage pools for storage of synthesized genetic data as the actual data.

20. The method of claim 19 wherein the oligonucleotide sequence is formatted in a Binary Aligned Map (BAM) file format, and further wherein the backup server comprises part of a restorer-based deduplication storage system, and uses variable length deduplication with delta encoding at the storage target storing the digital data; the method further comprising:
   initially loading the defined smart contract with an initial key-value pair managed using put and push methods;
   receiving a file stream with new data;
   dividing the new data into data chunks;
   pushing the new data to a ledger database using a put method in the smart contract; and
   using, for retrieval of the new data, a smart contract push function to retrieve a respective data chunk.

* * * * *